US011033615B2

(12) United States Patent
Thomas et al.

(10) Patent No.: US 11,033,615 B2
(45) Date of Patent: Jun. 15, 2021

(54) ZIKA VIRUS VACCINE AND METHODS OF PRODUCTION

(71) Applicants: The Government of the United States of America as Represented by the Secretary of the Army, Fort Detrick, MD (US); The Research Foundation For The State University of New York, Syracuse, NY (US)

(72) Inventors: Stephen J. Thomas, Skaneateles, NY (US); Timothy Endy, Manlius, NY (US); Kenneth H. Eckels, Rockville, MD (US); J. Robert Putnak, Silver Spring, MD (US); Richard Jarman, Frederick, MD (US); Rafael De La Barrera, Washington, DC (US)

(73) Assignees: The Government of the United States, As Represented by the Secretary of the Army Fort Detrick, Maryland, Fort Detrick, MD (US); The Research Foundation For The State University of New York Syracuse, New York, Syracuse, NY (US)

( * ) Notice: Subject to any disclaimer, the term of this patent is extended or adjusted under 35 U.S.C. 154(b) by 0 days.

(21) Appl. No.: 16/304,793

(22) PCT Filed: May 30, 2017

(86) PCT No.: PCT/US2017/035046

§ 371 (c)(1),
(2) Date: Nov. 27, 2018

(87) PCT Pub. No.: WO2017/210215

PCT Pub. Date: Dec. 7, 2017

(65) Prior Publication Data

US 2020/0179506 A1 Jun. 11, 2020

Related U.S. Application Data

(60) Provisional application No. 62/343,315, filed on May 31, 2016, provisional application No. 62/370,260, filed on Aug. 3, 2016.

(51) Int. Cl.

| | |
|---|---|
| ***A61K 39/00*** | (2006.01) |
| ***A61K 39/12*** | (2006.01) |
| ***C12N 7/00*** | (2006.01) |
| ***C07K 14/005*** | (2006.01) |
| ***A61K 39/39*** | (2006.01) |

(52) U.S. Cl.
CPC ................ *A61K 39/12* (2013.01); *C12N 7/00* (2013.01); *C12N 2770/24063* (2013.01); *C12N 2770/24134* (2013.01)

(58) Field of Classification Search
CPC ............ C12N 2770/24134; C12N 7/00; Y02A 50/392; A61K 39/12; A61P 31/14
See application file for complete search history.

(56) References Cited

U.S. PATENT DOCUMENTS

| | | | |
|---|---|---|---|
| 4,258,029 | A | 3/1981 | Moloney et al. |
| 4,912,094 | A | 3/1990 | Myers et al. |
| 5,057,540 | A | 10/1991 | Kensil et al. |
| 5,078,996 | A | 1/1992 | Conlon, III et al. |
| 5,723,127 | A | 3/1998 | Scott et al. |
| 6,207,646 | B1 | 3/2001 | Krieg et al. |
| 6,254,873 | B1 | 7/2001 | Putnak et al. |
| 6,309,650 | B1 | 10/2001 | Kim et al. |
| 8,691,961 | B1 | 4/2014 | Puffer et al. |
| 8,741,312 | B2 | 6/2014 | Lee et al. |
| 2011/0236421 | A1 | 9/2011 | Brown et al. |
| 2013/0022631 | A1 | 1/2013 | Ella et al. |
| 2013/0203151 | A1 | 8/2013 | Balsitis et al. |

FOREIGN PATENT DOCUMENTS

| | | | |
|---|---|---|---|
| CA | 2301000 | C | 7/2003 |
| CA | 2452545 | A1 | 7/2003 |
| EP | 1 724 338 | A1 | 11/2006 |
| WO | WO-92/19265 | A1 | 11/1992 |
| WO | WO-93/13202 | A1 | 7/1993 |
| WO | WO-2012/160199 | A1 | 11/2012 |
| WO | WO2012160199 | * | 11/2012 |
| WO | WO-2016/145149 | A1 | 9/2016 |
| WO | WO-2016/210127 | A1 | 12/2016 |
| WO | WO-2017/009873 | A1 | 1/2017 |

OTHER PUBLICATIONS

Cox et al., "Predicting Zika virus structural biolology: Challenges and opportunities for intervention", Antiviral Chemistry and Chemotherapy, 2015,24:118-126.*
Cox et al. "Predicting Zika virus structural biology: Challenges and opportunities for intervention",Antiviral Chemistry and Chemotherapy, 2015,24:118-126.*
A. Johansson, Y. T.-R. L. Mier, J. Reefhuis, S. M. Gilboa, S. L. Hills, "Zika and the Risk of Microcephaly," *N. Engl. J. Med.* 375: 2321-2334 (Dec. 15, 2016).
A. Rasmussen, D. J. Jamieson, M. A. Honein, L. R. Petersen, "Zika Virus and Birth Defects—Reviewing the Evidence for Causality," N. Engl. J. Med. 374: 1981 (May 19, 2016).
A. S. Fauci, D. M. Morens, "Zika Virus in the Americas—Yet Another Arbovirus Threat," *N. Engl. J. Med.* 374: 601 (Feb. 18, 2016).
C. Li et al., "Zika Virus Disrupts Neural Progenitor Development and Leads to Microcephaly in Mice," *Cell Stem Cell* 19(1): 120-126 (May 9, 2016).

(Continued)

*Primary Examiner* — Barry A Chestnut
(74) *Attorney, Agent, or Firm* — Faegre Drinker Biddle & Reath LLP

(57) ABSTRACT

The invention generally relates to a purified inactivated Zika virus (ZIKV), methods for producing the purified inactivated ZIKV, immunogenic compositions and vaccines comprising the purified inactivated ZIKV and methods for the prevention and/or treatment of infection by ZIKV.

17 Claims, 21 Drawing Sheets

(56) References Cited

OTHER PUBLICATIONS

D. H. Libraty et al., "A prospective nested case-control study of Dengue in infants: rethinking and refining the antibody-dependent enhancement dengue hemorrhagic fever model," *PLoS Med.* 6: e1000171 (Oct. 2009).

D. M. Dudley et al., "A rhesus macaque model of Asian-lineage Zika virus infection," *Nature Communications* 7: 12204 (2016).

Darlington S (Dec. 24, 2015). "Brazil warns against pregnancy due to spreading virus". CNN (available at https://www.cnn.com/2015/12/23/health/brazil-zika-pregnancy-warning/index.html). Retrieved Dec. 23, 2015.

Demicheli, P. Graves, M. Pratt, T. Jefferson, "Vaccines for preventing tick-borne encephalitis," *Cochrane Database of Systematic Reviews*, CD000977 (2000).

E. O. Erra, A. Kantele, "The Vero cell-derived, inactivated, SA14-14-2 strain-based vaccine (Ixiaro) for prevention of Japanese encephalitis," *Expert Rev. Vaccines* 14: 1167 (2015).

Edelman R., et al., "Phase II safety and immunogenicity study of a live chikungunya virus vaccine," *Am. J. Trop. Med. Hyg.* 62(6): 681-5 (2000).

G. Barba-Spaeth et al., "Structural basis of potent Zika-dengue virus antibody cross-neutralization," *Nature* 536(7614): 48-53 (Jun. 23, 2016).

Harrison V.R., et al., "Production and evaluation of a formalin-killed chikungunya vaccine," *J. Immunol.* 107: 643-47 (1971).

Hayes, E. B. (2009). "Zika Virus Outside Africa". *Emerging Infectious Diseases* 15 (9): 13471350. doi: 10. 3201/eidl5O9. 090442. PMC 2819875. PMJD 19788800.

J. Hombach, T. Solomon, I. Kurane, J. Jacobson, D. Wood, "Report on a WHO consultation on immunological endpoints for evaluation of new Japanese encephalitis vaccines," WHO, Geneva, Sep. 2-3, 2004. *Vaccine* 23: 5205 (Nov. 1, 2005).

J. J. Miner et al., "Zika Virus Infection during Pregnancy in Mice Causes Placental Damage and Fetal Demise," *Cell* 165: 1081 (May 19, 2016).

J. Mlakar et al., "Zika Virus Associated with Microcephaly," *N. Engl. J. Med.* 374: 951 (Mar. 10, 2016).

K. E. Stephenson et al., "Quantification of the epitope diversity of HIV-1-specific binding antibodies by peptide microarrays for global HIV-1 vaccine development," *J. Immunol. Methods* 416: 105 (Jan. 2015).

L. R. Petersen, D. J. Jamieson, A. M. Powers, M. A. Honein, Zika Virus. N. Engl. J. Med. 374: 1552 (Apr. 21, 2016).

Levitt N. H., et al., "Development of an attenuated strain of chikungunya virus for use in vaccine production," *Vaccine* 4(3): 157-62 (1986).

P. Abbink et al., "Construction and evaluation of novel rhesus monkey adenovirus vaccine vectors," *J. Virol.* 89: 1512 (Feb. 2015).

P. Brasil et al., "Guillain-Barre syndrome associated with Zika virus infection," *Lancet* 387: 1482 (Apr. 2, 2016).

P. Brasil et al., "Zika Virus Infection in Pregnant Women in Rio de Janeiro—Preliminary Report," *N. Engl. J. Med.* (Mar. 4, 2016).

P.P. Garcez et al., "Zika virus impairs growth in human neurospheres and brain organoids," *Science* 352: 816 (May 13, 2016).

R. A. Mason, N. M. Tauraso, R. O. Spertzel, R. K. Ginn, "Yellow fever vaccine: direct challenge of monkeys given graded doses of 17D vaccine," *Applied Microbiology* 25: 539 (Apr. 1973).

S. Fernandez et al., "An adjuvanted, tetravalent dengue virus purified inactivated vaccine candidate induces long-lasting and protective antibody responses against dengue challenge in rhesus macaques," *Am. J. Trop. Med. Hyg.* 92: 698 (Apr. 2015).

T. P. Endy et al., "Epidemiology of inapparent and symptomatic acute dengue virus infection: a prospective study of primary school children in Kamphaeng Phet, Thailand," *American J. Epidem.* 156: 40 (Jul. 1, 2002).

T. R. Kreil, I. Burger, M. Bachmann, S. Fraiss, M. M. Eibl, "Antibodies protect mice against challenge with tick-borne encephalitis virus (TBEV)-infected macrophages," Clin. Exp. Immunol. 110: 358 (Dec. 1997).

W. Dejnirattisai et al., "Dengue virus sero-cross-reactivity drives antibody-dependent enhancement of infection with zika virus," *Nat. Immunol.* 17:1102-1108 (Jun. 23, 2016).

W. Driggers et al., "Zika Virus Infection with Prolonged Maternal Viremia and Fetal Brain Abnormalities," *N. Engl. J. Med.* 374: 2142-2151 (Mar. 30, 2016).

X. Qian et al., "Brain-Region-Specific Organoids Using Mini-bioreactors for Modeling ZIKV Exposure," Cell 165: 1238-1254 (May 19, 2016).

International Report on Patentability dated Dec. 4, 2018 for PCT/US2017/035046.

International Search Report / Written Opinion dated Jul. 18, 2017 for PCT/US2017/035046.

International Preliminary Report on Patentability for PCT/US2017/035046, dated Dec. 4, 2018.

Cox D., Bryan, et al., "Predicting Zika virus structural biology: Challenges and oppotunities for intervention," Antiviral Chemistry and Chmotherapy, vol. 24, No. 3-4, 2015, 118-126.

Stettler, Karin, et al., "Specificity, cross-reactivity, and function of antibodies elicited by Zika virus infection," Science, vol. 353, No. 6301, Aug. 19, 2016, 823-826.

Taleb, Ziyad Ben, et al., "Syria: health in a country undergoing tragic transition," Int. J. Public Health (2015) 60 (Suppl 1): S63-S72.

International Search Report and Written Opinion dated Jul. 18, 2017 for PCT/US2017/035046.

Kandaswamy Sumathy, et al., "Vaccine Compositions," Jul. 16, 2015, 102 pages.

Putnak, J. Robert, et al., "An evaluation of dengue type-2 inactivated, recombinant subunit, and live-attenuated vaccine candidates in the rhesus macaque model," Vaccine 23 (2005) 4442-4452.

Martinez, Luis Javier, et al., "Safety and Immunogenicity of a Dengue Virus Serotype-1 Purified-Inactivated Vaccine: Results of a Phase 1 Clinical Trial," Am. J. Trop. Med. Hyg., 93(3), 2015, pp. 454-460.

Larocca, Rafael A., et al., "Vaccine Protection Against Zika Virus from Brazil," Nature, Aug. 25, 2016; 536(7617): 474-478.

Abbink, Peter, et al., "Protective Efficacy of Multiple Vaccine Platforms Against Zika Virus Challenge in Rhesus Monkeys," Science. Sep. 9, 2016; 353(6304): 1129-1132.

Monath, Thomas P., et al., "An Inactivated Cell-Culture Vaccine against Yellow Fever," The New England Journal of Medicine 2011; 364:1326-33.

Lyons, Arthur, et al., "A Phase 2 study of a purified, inactivated virus vaccine to prevent Japanese encephalitis," Vaccine 25 (2007) 3445-3453.

Dyer, Owen, "Zika vaccine could be in production by year's end, says maker," BMJ, 2016;352:i630.

Cugola, Fernanda R., et al., "The Brazilian Zika virus strain causes birth defects in experimental models," Nature. ; 534(7606): 2016, 267-271.

Cohen, Jon, "The race for a Zika vaccine is on," Science vol. 351, Issue 6273, Feb. 2016, 543-544.

Eckels, Kenneth E., et al., "Formalin-Inactivated Whole Virus and Recombinant Subunit Flavivirus Vaccines," Advances in Virus Research, vol. 61, 2003, pp. 395-418.

Dowd, Kimberly A., et al., "Rapid development of a DNA vaccine for Zika virus," Science, 2016, 10 pages.

Barouch, Dan H., et al., "Prospects for a Zika Virus Vaccine," Immunity 46, Feb. 21, 2017, pp. 176-182.

* cited by examiner

Flow Chart 2: ZIKV PIV GMP Production; Passage 1

ZIKV PRVABC59 ⇒ Vero-PM cells, 4 x 150 cm² flasks; harvest at 5-7 d; clarify and add 1:1 FBS ⇒ Aliquot 200 x 2 mL and freeze at -80°C Infectivity (PFU); sterility; sequence Flow Chart 3: ZIKV PIV GMP Production; Passage 2 Pre-Master Seed ZIKV PRVABC59, P-1 ⇨ Inoc Vero PM cells: 12 roller flasks; harvest 5-7 d → Infectivity (PFU)
⇨ Extract and purify RNA; freeze at -80°C → Assay RNA

ZIKA VIRUS VACCINE AND METHODS OF PRODUCTION

CROSS REFERENCE TO RELATED APPLICATIONS

This application is the National Stage of International Application No. PCT/US2017/035046, filed May 30, 2017, and claims benefit of U.S. Provisional Application No. 62/343,315 filed May 31, 2016 and U.S. Provisional Application No. 62/370,260 filed Aug. 3, 2016, both of which are incorporated by reference in their entirety.

STATEMENT REGARDING FEDERALLY SPONSORED RESEARCH

The invention was created with U.S. Government funding. The U.S. Government has rights in this invention.

FIELD

Described are immunogenic compositions, vaccines, and methods for immunization and protection (e.g., prophylaxis) against Zika virus (ZIKV) infection, treatment of ZIKV infection and symptoms, and immunization/protection/treatment of associated diseases, and clinical conditions. Also provided are purified, inactivated ZIKV compositions comprising virus that is re-derived from a ZIKV strain, and which confers an antibody titer sufficient for broad-based seroprotection against all strains of ZIKV.

BACKGROUND

Zika virus (ZIKV) is a member of the Flaviviridae virus family and the flavivirus genus. In humans, it causes a disease known as "Zika". It is related to dengue, yellow fever, West Nile and Japanese encephalitis viruses that are also members of the virus family Flaviviridae. Along with other viruses in this family, ZIKV is enveloped and icosahedral with a non-segmented, single-stranded, positive sense RNA genome. ZIKV is transmitted by mosquitoes and has been isolated from a number of species of the *Aedes* genus. The virus was first isolated in 1947 from a rhesus monkey in the Zika Forest of Uganda, Africa, and was isolated for the first time from humans in 1952 in Nigeria. Evidence of human infection has been reported from other African countries as well as in parts of Asia including India, Malaysia, the Philippines, Thailand, Vietnam, and Indonesia. In 2007 there was a Zika outbreak on the Micronesian Island of Yap, in 2013 there was an estimated 28,000 Zika cases in French Polynesia, and since early 2015 ZIKV has been infecting tens and perhaps hundreds of thousands in the Americas driving hundreds of travel related cases globally. Common symptoms of infection with ZIKV include mild headaches, maculopapular rash, fever, malaise, conjunctivitis, and arthralgia. Available data indicate approximately 20% of those infected will develop this mild disease phenotype. The recent outbreaks in French Polynesia and the Americas reveal the potential for very serious and sometimes fatal outcomes following congenital ZIKV infection (microcephaly) and serious neurologic sequelae following infection (Guillaing Barrè syndrome (GBS)) (22). Researchers estimate between 1-13% of ZIKV infections during the first trimester of pregnancy will result in microcephaly. In addition, ZIKV has been causally associated with intrauterine growth retardation, and other congenital malformations in both humans (15-18) and mice (19-21). Several reports have shown that ZIKV can infect placental and fetal tissues, leading to prolonged viremia in pregnant women (23) and nonhuman primates (24). ZIKV also appears to target cortical neural progenitor cells (19-21, 25 and 26), which likely contributes to neuropathology. The increased incidence of microcephaly temporally related to the introduction of ZIKV in the Americas resulted in the World Health Organization establishing a Public Health Emergency of International Concern (PHEIC). It is also because of these severe outcomes that a protective vaccine is required.

Currently there are no approved or licensed vaccines—or any known effective vaccines—to prevent ZIKV infection or disease. A number of Zika vaccine candidates in discovery and pre-clinical stages have been reported as "under development" in the public domain at scientific meetings. A search in PubMed using terms "Zika" and "vaccine" (accessed 29 May 2016) yielded 80 citations none of which described animal or human Zika vaccine data. The World Health Organization conducted a review of the Zika vaccine field (3 Mar. 2016) and concluded there were up to 18 active programs pursuing a number of different approaches to include purified inactivated (none others successful at that point), nucleic acid based vaccines (DNA, RNA), live vectored vaccines, subunit vaccines, VLP technologies and live recombinant approaches. There is an urgent need for a vaccine capable of inducing a protective immune response against infection from ZIKV, as well as compositions to treat ZIKV post-infection. Mechanisms of action of a prophylactic vaccine could include protecting against infection (failure of mosquito transmitted virus to replicate in the human abrogating infection), protecting against disease (mosquito transmitted virus replicates but at an insufficient level to cause disease), protecting against adverse neurologic sequelae (infection occurs but vaccine induced immunity impacts rate of adverse outcomes following infection), and/or protecting the fetus during maternal infection (infection during pregnancy occurs but vaccine induced immunity prevents fetal infection from taking hold). If vaccine-induced immunity kinetics are robust and rapid it is conceivable active immunization AFTER infection may be able to abrogate the adverse outcomes of ZIKV exposure (congenital, neurologic) before they take hold.

SUMMARY OF THE DISCLOSURE

A novel purified, inactivated ZIKV is described, including compositions and vaccines comprising it, methods for producing the same, and methods of using the same (e.g., generating an immune response in a subject at risk of infection and/or in need of preventative treatment, or raising antibodies in a subject, or alleviating symptoms of ZIKV in an infected subject, and the like).

ZIKV can be purified to be free of pathogens and adventitious agents. The ZIKV infectious virus particle can be purified away from the host cell proteins (demonstrated by known procedures such as gradient centrifugation and column chromatography). The level of purity is according to the guidelines of the U.S. Food and Drug Administration (FDA). The purified ZIKV is then inactivated using known chemical agents or any treatment which sufficiently preserves viral antigenicity and immunogenicity while destroying viral infectivity. The resultant purified, inactivated ZIKV is suitable for use as a vaccine component to generate an immune response but non-infective for ZIKV, or is part of a composition that can be used to generate antibodies in a subject exposed to it. It is quite safe for human and mammalian use. Other uses of the purified, inactivated ZIKV are described below.

The purified, inactivated ZIKV, when used in immunogenic compositions and vaccines, has a major advantage over attenuated virus vaccines and immunogenic compositions in that inactivated viruses are not infectious and therefore, cannot revert to virulence or cause disease. This is important when considering vaccination in known or potentially special populations such as those with immunodeficiencies (e.g., HIV) or those who are pregnant. Another advantage of inactivated over attenuated viruses is their potentially greater physical stability (e.g., to temperature changes) allowing easy and economical transport and storage of the vaccine and immunogenic compositions. In addition, inactivated viruses afford superior immunogenicity and greater protection against disease due to their preserved native conformation.

One composition can be a purified-inactivated vaccine (PIV) for ZIKV. The vaccines comprise, consist essentially of, or consist of one or more of the purified-inactivated ZIKV as described herein. The purified, inactivated ZIKV can be used to immunize mammals (including humans) to elicit high titers of virus neutralizing antibodies and protect the immunized mammal from disease caused by ZIKV. For example, a single immunization of the vaccine can be shown to provide 100% complete protection in susceptible mammals against challenge with ZIKV. Another example is wherein two doses are administered (e.g., a first dose, followed by a second dose 4 weeks later). A booster dose (second dose or more) may be useful for persons with recurrent infection risk. This is similar to the booster dose regimen associated with the PIV for the flavivirus, Japanese encephalitis (JEV). With the information known about the dosing and schedule for other PIV flavivirus vaccines—such as Japanese encephalitis and tick-borne encephalitis—someone skilled in this art can determine a safe and effective dose and schedule for this ZIKV PIV, as needed for persons of any age and size. Furthermore, potential immunologic correlates of protection are shown by the data below. The vaccine can be suitable for rapid immunization with the potential to break the cycle of viral transmission at the individual and population levels.

Optionally, this ZIKV vaccine (and any other compositions described herein) can be mixed with suitable adjuvants.

Compositions can comprise, consist essentially of, or consist of one or more of the novel purified, inactivated ZIKV as described herein. These are immunogenic compositions that are able to produce an immune response in a mammal—that is, they are able to induce the production of antibodies which recognize ZIKV, or are reactive with ZIKV.

The term "immunogenic" as used herein has its accepted well-known meaning in this art, relating to or denoting substances able to produce an immune response, the property enabling a substance to provoke an immune response, or the degree to which a substance possesses this property of immunogenicity. To that end, a composition can contain one or more of the purified-inactivated ZIKV as described herein, and an adjuvant, such as a pharmaceutical adjuvant. These compositions can be useful in methods to produce antibodies which recognize ZIKV in a host, when the compositions are administered by known means to the host.

A purified-inactivated ZIKV can be an inactivated strain of the purified Puerto Rican strain PRVABC59, described below. The purified-inactivated ZIKV can be any inactivated and purified strain of Zika. The methods for production and use as a vaccine would be applicable to strains other than the Puerto Rican strain. Additional strains are known currently, and some are described below.

Also provided is a method for producing purified, inactivated ZIKV for use in any of the vaccines and immunogenic compositions described herein. The method minimally includes the steps of purifying a selected ZIKV strain, and inactivating it. The method can include the following steps are:

(i) inoculating a cell culture with a ZIKV strain;
(ii) propagating the virus in the inoculated cell culture;
(iii) harvesting and isolating virus fluids from the inoculated cell culture to prepare a ZIKV concentrate; and preferably reducing the presence of host cell DNA, for instance by treatment of the harvest with a chemical agent such as benzonase;
(iv) purifying the ZIKV concentrate;
(v) inactivating the purified ZIKV; and
(vi) recovering the inactivated purified ZIKV.

Also provided is a purified, inactivated ZIKV generated by this method.

A ZIKV strain can be one that has first been subjected to passaging through an appropriate cell line—e.g., inoculating a cell culture with the strain, propagating the virus, harvesting the virus, and clarifying it. An appropriate cell line is any one that will permit adequate growth of the virus, and produce a viral product suitable for human use. For example, Vero cells are very suitable. Passaging cells at least 3 times produces an effective starting ZIKV strain (or "Master Seed"), although fewer or more passages can be done. The Master Seed can be frozen and tested and used for the purification-inactivation process described herein. In one embodiment described herein, where a Master Seed is produced by three passages, the purification steps (i)-(iii) of our process can be referred to as the fourth passage. The purification process can further include a re-derivation of the ZIKV strain by RNA transfection. In the preparation of the Master Seed, at the end of a second passage, RNA can be extracted and used in a third passage for transfection. This can be done using standard methods, as the strain is propagated in a cell line. This method results in reproducing a clean copy of the Zika virus within the cell line, and in so doing, removes possible contaminating adventitious agents, creating a purer strain. This RNA rederivation process reduces the risk of "carry-over" adventitious agents.

Inactivation can be done by contacting the purified ZIKV with a chemical inactivating agent, such as formalin or beta-propiolactone, or combinations of these, and other known agents.

The purified ZIKV strain PRVABC59 passaged 3 times is a particularly useful master seed that could be used for multiple vaccine lot productions at passage 4 in the purification-inactivation method. PRVABC59p-3 is a unique Master Seed, having a unique sequence and properties.

The methods described herein also entail using host cells that are useful for ZIKV vaccine production strains. An exemplary host cell line is Vero cells, although any cell line could be used that is permissive for growth of the ZIKV and yields product that is useful for ultimate human use.

Also contemplated are methods and kits to induce immune responses to ZIKV, or raise antibodies that recognize ZIKV, in a mammal (especially humans). The method comprises administering to a subject a composition comprising, including or consisting essentially of, one or more of the purified-inactivated ZIKV as described herein, in a pharmaceutically acceptable adjuvant, in an amount effective to cause an immune response (including raising antibodies that recognize ZIKV) in the subject. The composition may be a vaccine, and the immune response may be a protective immune response. Specifically, methods are provided for immunizing a mammal (especially a human) against ZIKV infection, which comprises administering to the mammal an amount of one or more of the vaccines disclosed herein to achieve effective immunization against ZIKV. Booster doses may be used, if needed. Administration may be by any known route, such as transcutaneous injection, intramuscular injection, intradermal injection, subcutaneous injection, intravenous injection, oral, or intranasal inoculation. A kit would contain one or more of the compositions described herein, and can include instructions for use.

Other uses of the purified, inactivated ZIKV as described herein include alleviating symptoms of ZIKV and/or treatment of ZIKV infection (e.g., post-infection). For example, in some vaccine embodiments, the ZIKV vaccine is effective to protect against disease prior to ZIKV exposure and infection, as well as alleviate disease and clinical symptoms associated with ZIKV following ZIKV exposure.

The method comprises administering to a subject infected with ZIKV a composition comprising, including or consisting essentially of, one or more of the purified-inactivated ZIKV as described herein, in a pharmaceutically acceptable adjuvant, in an amount effective to cause an immune response (including raising antibodies that recognize ZIKV) in the subject. The immune response effectively alleviates ZIKV symptoms or otherwise effectively treats ZIKV infection. The composition can be administered to an infected subject as soon as possible following initial infection, or at least between initial infection and development of congenital infection or onset of severe symptoms. Ideally, only one dose is needed to effect protection against Zika infection for mammals, including humans. An exemplary dosage schedule entails an initial dose, then a second (booster) dose about 4 weeks later. However, this schedule is exemplary only, and someone skilled in this art would be able to determine without undue experimentation if and when any second dose is needed.

Additional materials and methods are as follows:

1. A purified inactivated Zika virus (ZIKV).
2. A purified, inactivated, immunogenic ZIKV.
3. The purified, inactivated, immunogenic ZIKV of claim 2, wherein the ZIKV is PRVABC59, and the virus is purified and inactivated.
4. An immunogenic composition comprising a purified inactivated ZIKV and a pharmaceutically acceptable adjuvant.
5. An immunogenic composition comprising the purified, inactivated, immunogenic ZIKV of any of claim 2 or 3 and an acceptable adjuvant.
6. The immunogenic composition of claim 4, wherein the acceptable adjuvant is alum.
7. The immunogenic composition of claim 1, wherein the purified inactivated ZIKV is derived from ZIKV PRVABC59.
8. The immunogenic composition of claim 4, wherein the purified inactivated ZIKV is derived from ZIKV PRVABC59.
9. The immunogenic composition of any of claims 4 to 8, wherein the purified inactivated ZIKV is derived from Puerto Rico PRVABC59, Thailand SV0127/14, Philippine COC C 0740, or Brazil Fortaleza/2015, or other suitable strains.
10. A vaccine comprising a purified inactivated ZIKV and a pharmaceutically acceptable adjuvant.
11. A vaccine comprising the purified, inactivated, immunogenic ZIKV of claim 1A and a pharmaceutically acceptable adjuvant.
12. The vaccine of any of claim 10 or 11, wherein the pharmaceutically acceptable adjuvant is alum.
13. The vaccine of claim 10, wherein the purified inactivated ZIKV is derived from ZIKV PRVABC59.
14. The vaccine of claim 11, wherein the purified inactivated immunogenic ZIKV is derived from Puerto Rico PRVABC59, Thailand SV0127/14, Philippine COC C 0740, or Brazil Fortaleza/2015, or other suitable strains.
15. A method of producing antibodies which recognize ZIKV in a host comprising administering to the host a composition comprising the immunogenic composition of any of claims 4 to 9.
16. A method of inducing a protective immune response against a Zika virus (ZIKV) in a subject, comprising the step of administering to the subject the vaccine of claim 10.
17. A method of inducing a protective immune response against a Zika virus (ZIKV) in a subject, comprising the step of administering to the subject the vaccine of claim 11 or 14.
18. The method of any of claim 16 or 17, wherein the administering is via intramuscular injection, intradermal injection, subcutaneous injection, intravenous injection, oral administering, or intranasal administering.
19. A method treating or alleviating symptoms of ZIKV in a subject, comprising the step of administering to the subject the immunogenic composition of claim 4.
20. A method treating or alleviating symptoms of ZIKV in a subject, comprising the step of administering to the subject the purified, inactivated immunogenic composition of any of claim 5 or 8.
21. A medicament comprising the immunogenic composition of claim 4.
22. A medicament comprising the purified, inactivated immunogenic composition of any of claim 5 or 8.
23. A medicament comprising the vaccine any of claim 10 or 11.
24. A method of generating a purified inactivated ZIKV comprising the steps of:
    i) inoculating a cell culture with an amount of a ZIKV strain;
    ii) growing the inoculated virus in cell culture;
    iii) harvesting and isolating virus fluids from the inoculated cell culture to prepare a Zika virus concentrate;
    iv) purifying the ZIKV concentrate;
    v) inactivating the purified ZIKV; and
    vi) recovering the purified, inactivated ZIKV.
25. A method of generating a purified, inactivated, immunogenic Zika virus (ZIKV) comprising the steps of:
    i) inoculating a cell culture with an amount of a ZIKV strain;
    ii) growing the inoculated virus in cell culture;
    iii) harvesting and isolating virus fluids from the inoculated cell culture to prepare a Zika virus concentrate;
    iv) purifying the ZIKV concentrate;
    v) inactivating the purified ZIKV; and
    vi) recovering the purified, inactivated, and immunogenic ZIKV.

26. The method of claim 24, wherein the purified ZIKV is inactivated by contacting the ZIKV with a chemical inactivating agent.
27. The method of claim 26, wherein the chemical inactivating agent is formalin, beta-propiolactone or hydrogen peroxide.
28. The method of claim 25, wherein the ZIKV strain used in step (i) has been passaged at least 3 times in a host cell line.
29. The method of claim 26, wherein the ZIKV strain is Puerto Rico PRVABC59, Thailand SV0127/14, Philippine COC C 0740, or Brazil Fortaleza/2015, or other suitable strains.
30. The method of claim 28, wherein after passaging 2 times the ZIKV is rederived by RNA transfection in a third passage.
31. A purified inactivated ZIKV produced by the method of claim 25.
32. The use of a purified, inactivated, immunogenic ZIKV of claim 2 for the manufacture of a medicament for the prevention of a Zika virus infection in a host or for the prophylaxis of a Zika infection in a host believed to have been exposed to a Zika virus.
33. A method treating or alleviating symptoms of ZIKV in a subject, comprising the step of administering to the subject the immunogenic composition of any of claims 4 to 9.
34. A method of generating a purified inactivated immunogenic Zika virus (ZIKV) comprising the steps of:
    inoculating a cell culture with an amount of a ZIKV strain, wherein the Zika strain is Puerto Rico PRVABC59, Thailand SV0127/14, Philippine COC C 0740, or Brazil Fortaleza/2015, or other suitable strains.

culturing the inoculated virus in cell culture;
    harvesting and isolating viral fluids from the inoculated cell culture to prepare a ZIKV concentrate;
    purifying the ZIKV concentrate;
    inactivating the purified ZIKV concentrate producing a purified, inactivated immunogenic ZIKV concentrate; and
    recovering the purified, inactivated immunogenic ZIKV concentrate.

35. The method of claim 34, wherein the purified ZIKV is inactivated by contacting the ZIKV with 0.05% formalin at 22° C. until complete inactivation can be demonstrated.
36. The method of claim 35, wherein the purified ZIKV is inactivated for about 6 to about 7 days.
37. The method of claim 25, wherein the ZIKV strain used in step (i) is a low passage of less than 10 passages in a host cell line.
38. The method of claim 34, wherein the ZIKV is passaged one to two times and then the ZIKV is rederived by RNA transfection of an uninfected cell culture in a third passage.
39. A purified inactivated immunogenic ZIKV vaccine produced by any of the methods of claims 34-38.

Other aspects will be apparent to one of skill in the art upon review of the description and exemplary depictions that follow.

BRIEF DESCRIPTION OF THE DRAWINGS

For the purpose of illustrating the disclosure, there are depicted in the drawings certain features of the aspects and embodiments of the disclosure. However, the disclosure is not limited to the precise arrangements and instrumentalities of the aspects depicted in the drawings.

FIG. 7 shows the results of testing of the purified, inactivated ZIKV vaccine using PRVABC59 as the vaccine strain, in mice. Balb/c mice (N=5/group) received a single immunization by the intramuscular (IM) or subcutaneous (SQ, also s.c.) routes with 1 μg PIV vaccine with alum or alum alone and were challenged at week 4 by intravenous injection with $10^5$ viral particles (VP)($10^2$ plaque-forming units (PFU)) of ZIKV-BR (Brazilian isolate). In FIG. 7*a*, the X axis is the vaccine or sham delivered IM or SQ, and PIV delivered IM or SQ. The Y axis shows the log titer of antibodies against the ZIKV Env gene determined by ELISA. In FIG. 7*b*, the X axis is the protected (no viremia) versus not protected (measurable viremia) after challenge with ZIKV. The Y axis is the same as FIG. 7*a*. This is significant data, because it shows that the sham does not induce an antibody response while the PIV does induce an antibody response. It also shows that the PIV given by the IM route is superior to the PIV given by the SQ route. Anti-ZIKV antibody titers were correlated with protection following challenge.

FIG. 8 shows the results of testing a vaccine prepared by the method described herein, using PRVABC59 as the vaccine strain, in mice. The terms are the same as used in FIGS. 7*a* and 7*b*. In this figure, serum viral loads are shown following ZIKV-BR challenge. The X axis is the number of days after challenge, and the Y axis is the quantity of ZIKV expressed as copies of viral particles per ml of serum tested. The X and Y axis together detail the kinetics of viral replication following challenge. Each graph in FIG. 8 represents a different treatment group. Alum alone is used as the sham compared to ZIKV PIV administered in the muscle or subcutaneously. These results are significant, because they show that the PIV induces antibody production, and that the antibodies protect against ZIKV (i.e., induce protective immunity). The results for the protected mice versus the non-protected mice are statistically significant. With the sham there is almost completely unrestricted viral replication in the mice while in the ZIKV PIV group viremia is 100% prevented in the IM recipients, and 3 out of 5 are 100% protected in the SQ group (and the 2 which had viremia had significantly reduced viremia in terms of quantity and duration of viremia). Taken together, the results shown in FIGS. 7*a-b* and 8 show that the ZIKV PIV induces antibodies in mice, and that these antibodies prevent viral replication after challenge—even after challenge with a different strain of ZKIV than used to make the vaccine.

(FIG. 9A) Env-specific ELISA titers and (FIG. 9B) ZIKV-specific microneutralization (MN50) titers following immunization of rhesus monkeys by the SQ route with 5 μg ZIKV PIV vaccine at weeks 0 and 4 (gray arrows). The maximum measurable log MN50 titer in this assay was 3.86. Cellular immune responses by IFN-γ ELISPOT assays to prM, Env, Cap, and NS1 at (FIG. 9C) week 2 and (FIG. 9D) week 6. Gray bars reflect medians.

(FIG. 11A) Env-specific serum ELISA titers and (FIG. 11B) ZIKV-specific microneutralization (MN50) titers in serum from recipient Balb/c mice (N=5/group) 1 hour following adoptive transfer of 5-fold serial dilutions (Groups I, II, III, IV) of IgG purified from PIV vaccinated rhesus monkeys or sham controls. (FIG. 11C) shows plasma viral loads in mice following challenge with $10^5$ VP ($10^2$ PFU) ZIKV-BR. (FIG. 11D, E) Immune correlates of protection. Gray bars are medians. P-values indicate statistical significance by t-tests.

(FIG. 12A) ZIKV-specific microneutralization (MN50) titers in serum from recipient rhesus monkeys (N=2/group) 1 hour following adoptive transfer of 5-fold dilutions (Groups I, II) of IgG purified from PIV-vaccinated rhesus monkeys or sham controls. (FIG. 12B) Plasma viral loads in rhesus monkeys following challenge with $10^6$ VP ($10^3$ PFU) ZIKV-BR. Gray bars show medians.

DETAILED DESCRIPTION

Figure 1:
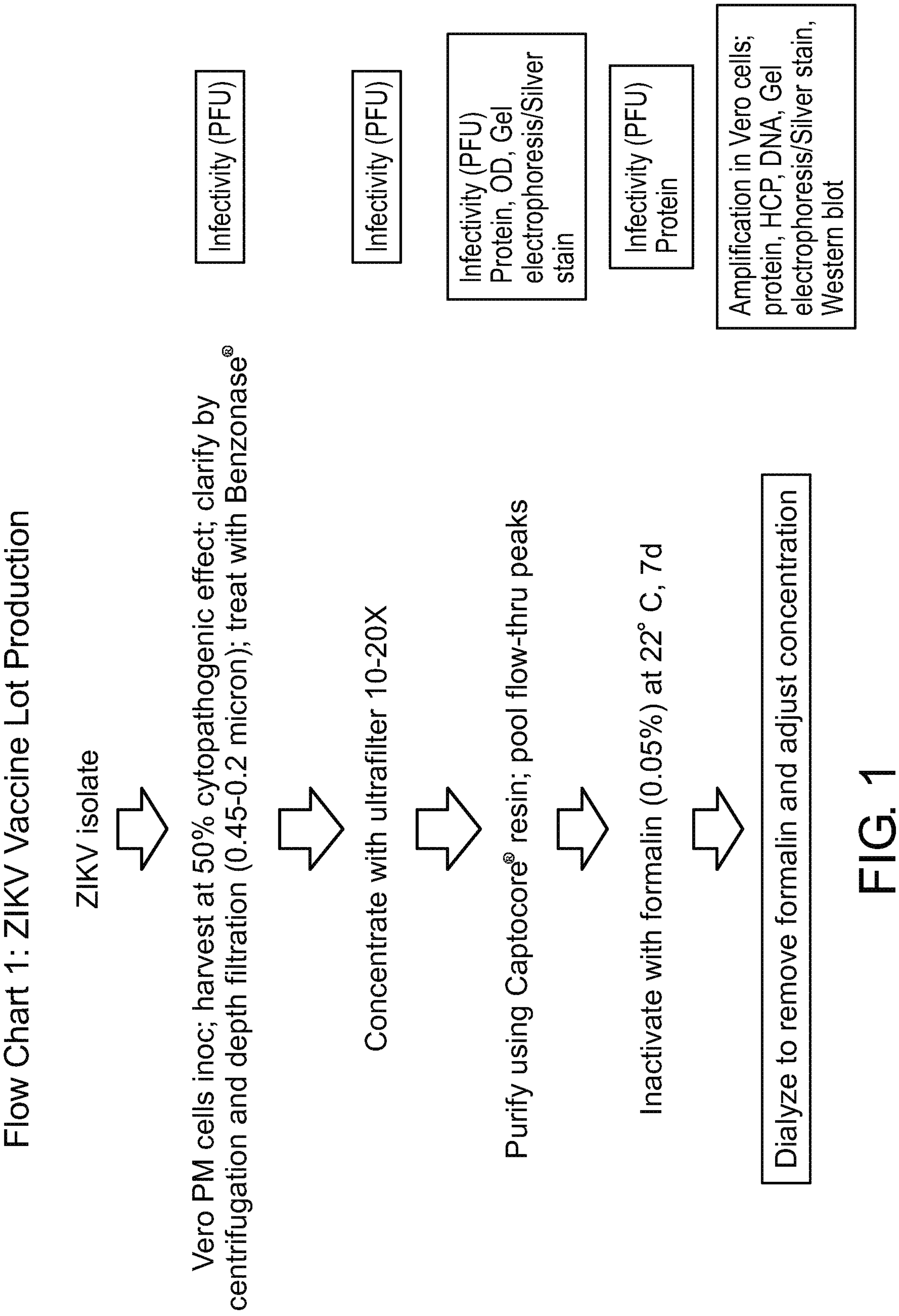
FIG. 1 provides a generalized process flow chart for one method of production of purified inactivated ZIKV vaccine.

Before continuing to describe various aspects and embodiments in further detail, it is to be understood that this disclosure is not limited to specific compositions or process steps, as such may vary. It must be noted that, as used in this specification and the appended claims, the singular form "a", "an" and "the" include plural referents unless the context clearly dictates otherwise. Unless defined otherwise, all technical and scientific terms used herein have the same meaning as commonly understood by one of ordinary skill in the art. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry and Molecular Biology, Revised, 2000, Oxford University Press, provide one of skill with a general dictionary of many of the terms used herein.

A "vaccine" as referred herein is defined as a pharmaceutical or therapeutic composition used to inoculate an animal in order to immunize the animal against infection by an organism, such as ZIKV. Vaccines typically comprise one or more antigens derived from one or more organisms (ZIKV) which on administration to an animal will stimulate active immunity and protect that animal against infection with these or related pathogenic organisms.

By "viruses" is meant different strains (genotypes) of the ZIKV virus, causing the same disease or responsible for different diseases. It is understood that the vaccines can combine different strains of ZIKV viruses.

The term "pharmaceutically (or pharmacologically) acceptable" means that its administration can be tolerated by a recipient patient or subject. An agent is physiologically significant if its presence results in a detectable change in the physiology of a recipient patient. The compounds herein can be formulated according to known methods to prepare pharmaceutically useful compositions, whereby these materials, or their functional derivatives, are combined in an admixture with a pharmaceutically acceptable adjuvant vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of adjuvant.

By "purified" virus, it is meant ZIKV viral particles separated from host cell proteins and DNA.

By "adventitious agent, it is meant a contaminant that enters the passage or production stream beginning with the isolate at the start of the process.

The term "consisting essentially of" is intended to encompass the specified materials, compositions and methods herein and those that do not materially affect the basic and novel characteristic(s) of the materials, compositions and methods. Basic and novel characteristics of the compositions and methods include the purified, inactivated ZIKV, as produced by the process described herein, and derived from the ZIKV strains designated as the Puerto Rican strain and the Thai strain. An exemplary strain is designated PRV-ABC59 (or the Puerto Rican strain, or ZIKV-PR). It was obtained from an outbreak in the Americas, which had significant levels of resulting microcephaly and Guillain-Barre syndrome, so had particular need for a vaccine. In addition, this strain had a passage history that is acceptable for vaccine development, and had good early success in yield studies in laboratories. However, the methods for producing and using the PIV described herein would be applicable for any known strain of ZIKV. The strains are sufficiently homologous that the vaccine would be made substantially the same way, and used substantially the same way, for any ZIKV strain. The basic and novel characteristics also include the use of the purified, inactivated ZIKV as a vaccine or in an immunogenic composition, and all other related uses as described herein. The use of the purified, inactivated ZIKV is effective for the purposes described herein, alone or in the presence of other ingredients or components. Thus, the presence of other ingredients or components does not materially affect the basic and novel characteristics of the compositions described or methods of making and using the compositions described herein. When used in connection with our novel methods of use, the phrase "consisting essentially of" is a modifier of method steps, such as to include only steps which do not materially affect the basic and novel characteristics of the claimed method.

The inventors have developed a purified inactivated vaccine (PIV) that is effective in immunizing a subject against ZIKV infection, and/or preventing disease and clinical symptoms associated with or caused by ZIKV infection. Immunogenic compositions and vaccines comprising the inactivated virus can provide for a global vaccine protecting the recipient from disease caused by any ZIKV strain from any part of the world—including but not limited to the Puerto Rican strain, the Thailand strain, the Philippine strain and the Brazilian strain, as well as any strains circulating in the Americas, Africa and Asia. These strains are generally accessible, and most of the sequences of these strains have been published. The Asian and America strains are >99% homologous based on currently available data. Also, our mouse experiment detailed herein also supports that the strains are quite homologous—as shown, the mouse challenged with a Brazilian strain was 100% protected by the ZIKV vaccine made with Puerto Rican strain. The non-human primate studies described below show that rhesus monkeys were 100% protected by the ZIKV vaccine. The mouse and non-human primate data track each other completely and yield the same conclusions: anti-Zika antibodies protect against infection in mice and non-human primates. ZIKV PIV generates robust anti-Zika antibodies in both models. Based on these models, and what is already known in the field of flavivirus PIVs, extrapolation to human use is reasonable for safe and effective dosages (e.g., a single dose, or a booster dose at 4 weeks as described below).

Other purified inactivated viruses have been successfully employed as vaccines against other viral agents including, for example, Japanese encephalitis (JE), and tick borne encephalitis, and have been shown experimentally to have promising results in other diseases such as dengue (DENV) and yellow fever (YFV). As is well understood by persons working in this field, each of these pathogens has a distinctive clinical disease associated with it. Zika is unique in that there are congenital and neurologic outcomes believed to result from autoimmune versus direct viral effects, and additionally, a purified inactivated whole virus is advantageous because of its potential for a superior safety profile in special populations like pregnant women. In addition, regarding DENV, the inactivation kinetics (rate of inactivation) are different—only about 1 day is needed to inactivate ZIKV, whereas 2 days are needed for DENV.

A purified, inactivated vaccine (PIV) provides many advantages relative to other types of immunogenic products, and particularly attenuated, live viruses. Such advantages of a PIV include an additional margin of safety by virtue of the absence of genetic reversion to a virulent, wild type virus, potentially lower acute reactogenicity following vaccination, rapid immunization timelines, potential to co-administer with other vaccines, and the like. Thus, a vaccine comprising a purified, inactivated ZIKV such as described herein can have the advantages of (1) an excellent safety profile with no risk for reversion and (2) the potential to confer protective immunity more quickly than live attenuated vaccines without their undesirable side effects. Not only are inactivated vaccines more stable and safer than live vaccines, they are usually easier to store and transport as they do not require refrigeration. Further such compositions can be easily stored and transported in a freeze-dried form, which provides for greater accessibility to people in developing countries.

The vaccines and immunogenic compositions of ZIKV can be made using the following novel method. A live ZIKV is purified so as to remove all pathogens and adventitious agents. The ZIKV can be purified so that no other impurities are present in the final product which could compromise the safety of the vaccine or immunogenic composition, or interfere significantly with the immunologic effect and subsequent protective outcome. The ZIKV strain also can be rederived by RNA transfection in a desired passage (e.g., p-3) so that the possibility of adventitious agents and other contamination is reduced. The product of rederivation is further purified to eliminate host cell protein and DNA. The purified ZIKV (still technically having infective properties) is then inactivated so that it is not capable of infecting a host with ZIKV but still has sufficient viral antigenicity and immunogenicity to induce an immunogenic response in a host and/or generate an antibody response reactive to ZIKV—not infective but strongly immunogenic. For the vaccine embodiments, the purified, inactivated ZIKV is capable of inducing a protective response.

Figure 7A:
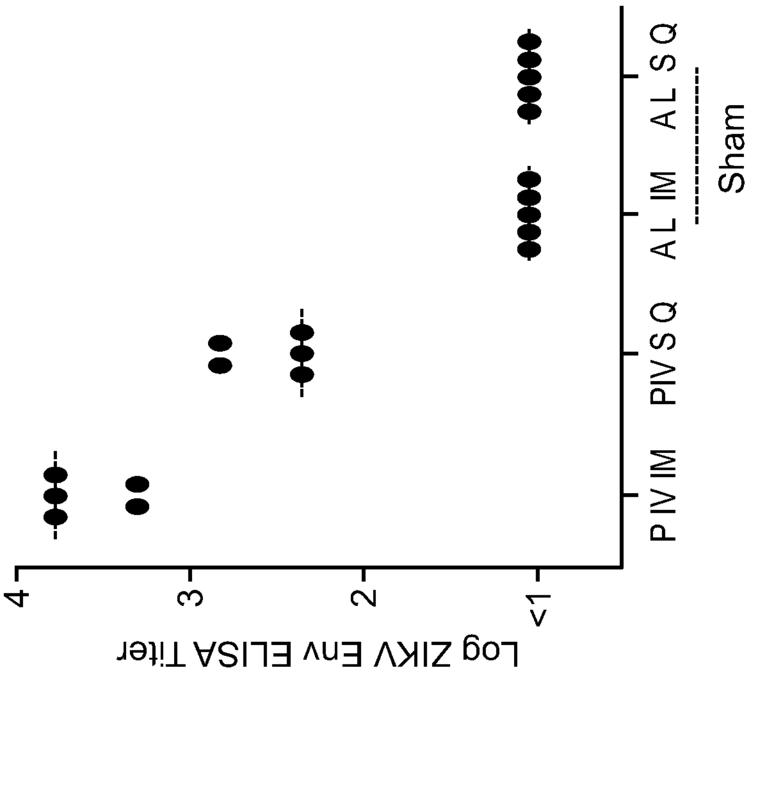
In FIG. 7*a*, humoral immune responses were assayed at week 3 following vaccination by Env-specific ELISA.

Any ZIKV strain or isolate or derivative may be used. Examples of ZIKV strains include the isolates known as Thailand SV0127/14, Philippine COC C 0740, Brazil Fortaleza/2015, and Puerto Rico PRVABC59, although more are known. Complete genome sequences of the Zika virus strains isolated from the blood of patients in Thailand in 2014 and in the Philippines in 2012 are provided in for example the article and associates documents of Ellison et al., "Completed Genome Sequences of Zika Virus Strains Isolated from the Blood of Patients in Thailand in 2014 and the Philippines in 2012," Genome Announcements 4(3): e00359-16. All ZIKV strains would be useful in the compositions described herein, in all of its embodiments. The ZIKV strain may be live or attenuated as a starting material. An exemplary strain is the Puerto Rican strain PRVABC59. When inactivated, the ZIKV strains are effective in immunogenic compositions and vaccines. PRVABC59 demonstrated good potential as a vaccine, and as described in FIGS. 2-5, PRVABC59 was used to prepare an effective vaccine. FIGS. 7 and 8 show the results of successful tests of this vaccine in mice. In particular, a potential mechanistic correlate of protection is shown in the successful use of the Puerto Rican strain vaccine to protect a mouse challenged with the Brazilian strain. Japanese encephalitis, yellow fever, and tick borne encephalitis vaccines have also demonstrated validated correlates of protection which are antibody-based (ELISA or neutralizing). FIGS. 9-19 show the results of successful tests of this vaccine in rhesus monkeys. Immunogenicity and protective efficacy of the PIV is demonstrated. All PIV vaccinated animals showed complete protection against ZIKV challenge.

Purification of the ZIKV may be performed by physical or chemical techniques or any combinations thereof that are routinely used in the art. Physical methods utilize the physical properties of the virus such as density, size, mass, sedimentation coefficient, and the like, and include but are not limited to, ultracentrifugation, density gradient centrifugation, ultrafiltration, size-exclusion chromatography, and the like. Chemical purification can employ methods such as adsorption/desorption through chemical or physiochemical reactions such as ion exchange chromatography, affinity chromatography, hydrophobic interaction chromatography, hydroxyapatite matrix, precipitation with inorganic salts such as ammonium sulfate, and the like.

Inactivation of the ZIKV can be done by any method generally known in the art, as long as the end product is a non-infectious Zika virus that retains high immunogenicity and preserves viral antigenicity. For instance, the ZIKV may be rendered non-infectious by killing/inactivating the virus by heat, gamma irradiation, UV light, or by contact with a chemical agent, such as formalin or beta-propiolactone (BPL), glutaraldehyde, N-acetylethyleneimine, binary ethyleneimine, tertiary ethyleneimine, ascorbic acid, caprylic acid, psolarens, detergents including non-ionic detergents, and the like. The chemical inactivating agent is added to a virus suspension in an amount effective to inactivate the virus, under conditions that retain high immunogenicity of the vaccine preparation. An inactivation temperature can be 22° C.

For example, inactivation with formalin can be performed at 4-22° C. for a time sufficient to achieve complete inactivation of infectivity while the virus particles maintain a protective response (remain immunogenic when administered to a host animal), considering also the recommended three-fold safety margin since formalin inactivation is non-linear. Inactivation can be performed for 2 or more days, but generally less than 10 days. For example, inactivation with formalin can be performed for about 7 days at 22° C. Optional filtration through a 0.22 μm filter may be performed, and the filtered material transferred to a fresh container at 48 hrs to remove virus aggregates resistant to inactivation. In some embodiments, BPL, which may be faster and exhibit more linear kinetics, may be used for inactivation. Typically, the inactivating agent is neutralized (e.g., with sodium bisulfite in the case of formalin) or removed by diafiltration.

The purification—inactivation method for ZIKV can include at least the following steps:

(i) inoculating a cell culture with a ZIKV strain (e.g., a Master Seed or a strain that has been passaged at least 3 times);

(ii) propagating the virus in the inoculated cell culture;

(iii) rederivation of the strain the transfection to make a Master Seed;

(iv) preparing a vaccine lot by inoculation with the Master Seed, and harvesting and isolating virus fluids from the inoculated cell culture to prepare a ZIKV concentrate;

(v) treating clarified ZIKV harvest with enzymes or other chemicals that degrade host cell DNA to acceptable levels;

(vi) concentrating ZIKV virus using an ultrafilter;

(vii) purifying the ZIKV concentrate to remove host cell contaminants;

(viii) inactivating the purified ZIKV; and (ix) recovering the inactivated purified ZIKV.

Rederivation of the ZIKV—especially for the vaccine Master Seed—by RNA transfection can be an important step, because this helps provide for a composition/vaccine that is free from any contaminating adventitious agents that may otherwise induce an adverse event or side effect when administered to a subject, and also provides an additional margin of safety. Besides ensuring purity, it allows for absolute traceability of the viral strain. At the end of a second passage, RNA can be extracted, and in after a third passage the RNA is used for transfection. The passaged ZIKV strain may be re-derived by RNA transfection using any standard method known in the art, in a suitable cell line such as, for example, Vero cells that have been certified for vaccine production. The re-derived virus may be used to produce a vaccine master seed lot and/or a working seed lot. By "master seed" is meant a seed lot that can be used for vaccine lot production, and it helps ensure the reproducibility of vaccine lot production.

The purified, inactivated ZIKV is useful to prepare compositions, such as vaccines, that are effective to generate a prophylactic immune response against ZIKV infection. The compositions, including vaccines, may also (or alternatively) be effective to generate a therapeutic immune response against ZIKV infection. For example, ZIKV is propagated to high titers in cell lines suitable for making human-use products. Specifically, ZIKV is passaged and replication-optimized (e.g., in Vero monkey kidney cells), then purified using column chromatography or other purification methods and inactivated with, for example, formalin. The final PIV is adjuvanted with alum or other adjuvants that enhance immunogenicity. Animals including mice and non-human primates that receive injections of the PIV will mount antibody responses that are protective. If desired, an immune response may be induced in a virus naïve subject.

As an example of the method of producing the purified, inactivated ZIKV, the following protocol was used. The starting material was a strain of ZIKV adapted to grow in Vero cells by 2-3 cell serial passages at a low multiplicity of infection (MOI). Multiple strains of ZIKV were screened with the most infectious being selected for development. Specifically, the ZIKV isolates that were tested include Thailand SV0127/14, Philippine COC C 0740, Brazil Fortaleza/2015, and Puerto Rico PRVABC59.

The higher-yielding strains are preferred. For instance, the preferred minimum yield in order to be further down-selected is 7 logs output, after the respective strain is transfected into the host cell. However, as is well known in the art, there are procedures to increase yield so this list is not exhaustive of the ZIKV strains that can be used to produce the compositions and vaccines described herein.

The strain selected was the Puerto Rico strain, PRV-ABC59. The Puerto Rico strain initially showed the best yield.

As an example of screening ZIKV isolates for use in our purification-inactivation process, the following passaging protocol can be used. Monolayers of Vero-PM cells (<p-146) can be prepared in 25 $cm^2$ flasks. The isolate can be thawed and diluted to an MOI of 0.01 in EMEM diluent (if titer is known). If titer is not known, a 1:100 dilution for inoculation can be made. Flasks of 2×25 $cm^2$ can be inoculated using 1.0 mL inoc; let adsorb for 1 h at 35° C.; then 7.0 mL EMEM maintenance medium can be added to each flask (Safe Operating Procedure SOP M-093-xx). Cytopathic effects (CPE) are daily observed and recorded. From each flask, 0.5 mL is removed daily until CPE has progressed to 3-4+. A sample can be added to an equal volume of fetal bovine serum (FBS) and frozen at −80° C. All samples taken can be assayed on Vero-WHO cells using a standard SOP for flavivirus plaque assay (SOP QC-145-xx).

In the method of ZIKV purification and inactivation, the selected ZIKV strain(s) was re-derived by RNA transfection using standard methods in a suitable cell line (e.g., Vero cells that have been certified for vaccine production) so as to eliminate potential adventitious agents. The re-derived virus was used to produce vaccine master seed lots. For vaccine lot manufacture the certified Vero cells grown in roller bottles, cell factories, or suspension cultures were infected with the ZIKV master seed at a suitable MOI (e.g., 0.1 to 0.001). After infection the cell culture fluids containing the virus were harvested based on the development of cytopathology (e.g., 50% or more cells showing cytopathic effects, CPE) and/or viral antigen yields measured by a suitable assay such as virus hemagglutination or ELISA. Depending upon the infection time course and the amount of cytopathology the virus can also be harvested continuously or at intervals throughout the infection cycle with replacement of removed culture medium. The collected bulk supernatant harvests were pooled and concentrated approximately 10 to 20-fold by a suitable method, (e.g., tangential flow ultrafiltration using an appropriate membrane pore size to retain the virus and remove small MW contaminants). The virus concentrate was then subjected to Benzonase® (Millipore Sigma) treatment or protamine sulfate precipitation to remove residual host cell nucleic acids and contaminating cellular proteins. The concentrated, treated virus pool was then purified by a suitable method such as density gradient centrifugation, rate zonal centrifugation, continuous flow centrifugation, or column chromatographically, and the virus peak fractions were identified by HA or ELISA or optical density, and pooled. The purified virus concentrate was quantified for protein, infectivity and viral and host cell antigen content and host nucleic acids.

Inactivation of the purified virus was performed by a suitable method that preserves viral antigenicity such as formalin or beta-propriolactone (BPL). For example, inactivation with formalin can be performed at 4° C. to 22° C. for a time sufficient to achieve complete inactivation of infectivity, considering also the recommended three-fold safety margin since formalin inactivation is non-linear, with filtration through a 0.22 μm filter and transfer to a fresh container at 48 hrs to remove virus aggregates resistant to inactivation. Similarly, BPL, which is faster and exhibits more linear kinetics, can also be used. The inactivating agent is typically neutralized (e.g., with sodium bisulfite in the case of formalin) or removed by diafiltration.

Bulk vaccines can be tested for sterility, protein, antigen and nucleic acid content using established assays. Residual infectivity can be assayed by inoculation of approximately 5% of the lot volume onto Vero cell cultures, or another suitable cell line, followed by incubation for a sufficient time to amplify any residual infectious virus present, which can then be detected by IFA directly on the cells or by a plaque assay of the culture supernatants. Following inactivation the bulk vaccines can be mixed with suitable excipients and/or stabilizers and stored frozen (e.g., −20° C. to −80° C. prior to formulation). Inactivated ZIKV bulk can be diluted to a protein concentration that will be suitable for a human immunizing dose. Final, vialed vaccine can be tested for purity, identity, osmolality, endotoxin, and sterility by various, standardized assays.

The method can be useful to produce a purified, inactivated ZIKV that may be used for production of vaccine lots. The method entails infection of a suitable cell line for vaccine manufacture—for example, certified Vero cells grown in roller bottles, cell factories, or suspension cultures can be infected with the ZIKV master seed at a suitable MOI (e.g., 0.1 to 0.001). By “master seed” is meant the seed that is suitable for use for multiple lots of vaccine lot production, it can be the result of our process that includes RNA transfection. It is thoroughly tested for adventitious agents and other contaminants. After infection the cell culture fluids containing the virus can be harvested based on the development of cytopathology (e.g., 50% or more cells showing cytopathic effects, CPE) and/or viral antigen yields measured by a suitable assay such as virus hemagglutination (HA) or ELISA. Depending upon the infection time course and the amount of cytopathology the virus may also be harvested continuously or at intervals throughout the infection cycle with replacement of removed culture medium. The collected bulk supernatant harvests can be pooled and concentrated approximately 10 to 20-dfold by a suitable method, (e.g., tangential flow ultrafiltration using an appropriate membrane pore size to retain the virus and remove small MW contaminants). The virus concentrate can be subjected to a treatment that removes residual host cell nucleic acids and contaminating cellular proteins such as, for example, Benzonase® treatment or protamine sulfate precipitation. The concentrated, treated virus pool may then be purified by a suitable method such as density gradient centrifugation, rate zonal centrifugation, continuous flow centrifugation, or column chromatographically, and the virus peak fractions may be identified by optical density (OD), HA or ELISA, and pooled. The purified virus concentrate can be quantified for protein, infectivity and viral and host cell antigen content and host nucleic acids.

Bulk vaccines may be tested for sterility, protein, antigen and nucleic acid content using established assays. Residual infectivity can be assayed by inoculation of approximately 5% of the lot volume onto Vero cell cultures, or another suitable cell line, followed by incubation for a sufficient time to amplify any residual infectious virus present, which can then be detected by IFA directly on the cells or by plaque assay of the culture supernatants. Following inactivation the bulk vaccines can be mixed with suitable excipients and/or stabilizers and stored frozen (e.g., −20° C. to −80° C. prior to formulation). Inactivated ZIKV bulk may be diluted to a protein concentration that is suitable for an immunizing dose in a subject (e.g., a mammal such as a human). The final, vialed vaccine may be tested for purity, identity, osmolality, endotoxin, and sterility by various, standardized assays generally known in the art.

Immunogenic potency of bulk vaccine lots and the final formulation can be tested by administering the vaccines to mice. Typically, groups of ten 5-6 week-old, female, Swiss-ICR mice receive serially graded doses ranging from about one nanogram to one microgram of vaccine, as required to reach an endpoint, in a 0.2 ml intramuscular or subcutaneous dose. A corresponding control group receives saline or saline plus adjuvant, as appropriate. Mice are typically boosted once; this can be done on day 14 or 28 after priming, and then blood is collected one to two weeks later. The sera from individual mice are assayed for virus neutralizing antibodies and the vaccine median immunizing dose (ID50) is calculated. In this way vaccine potency and stability may be monitored periodically.

An animal efficacy study is designed to demonstrate that the vaccine is safe and has the potential for clinical benefit in human populations. Animal models may be infection models or disease models. If the animal experiences disease similar to humans this is a disease model and is desired. In the event animals do not experience disease manifestations after exposure but viral replication (viremia) is measurable it is possible to extrapolate animal results to potential outcomes in humans (prevent viremia=prevent disease). Therefore, if vaccination does not cause any adverse events in the animal and induces an effective immune response (neutralizing antibodies) which protects against a live virus challenge in comparison to a placebo or another control this is typically supportive data to advance to human trials. This testing may be necessary before a vaccine can progress to a clinical trial. Typically, such experiments are best performed in a non-human primate infection model (e.g., rhesus macaques) with the primary endpoints being the measurement of virus neutralizing antibodies after vaccination and the measurement of protection against challenge with an attenuated or wild type ZIKV strain. Protection can be assessed by a disease surrogate such as circulating virus (viremia) after virus challenge with a near-wild-type (low passage) strain of ZIKV. Various vaccine doses and immunization schedules can also be tested in the experiment. Group sizes of 5 to 10 are suitable for a pilot study. For example, using Fisher's Exact Test with alpha=0.05 (2-sided) and n=5 animals per group: for 100% vs. 0%, or 100% vs. 5%, the power is about 80%. Responses can be compared and contrasted for individual animals and among groups using standard statistical methods. For example, log-transformed antibody and viremia titers can be analyzed by ANOVA. Fisher's exact test can be used to compare rates of seroconversion to each virus antigen and viremia rates among vaccine groups and placebo controls. A one-way analysis of variance with a contrast test for trend may be used to assess differences in antibody or viremia titers among groups. To stabilize the variance the analysis is conducted on the logs of the quantified responses. A test for trend using the logistic model can be used to assess differences in the proportion of seroconverters.

Reactogenicity of the vaccines disclosed herein may be monitored and evaluated as may be necessary. A reactogenicity event is typically identified as an adverse event that is commonly known to occur for the candidate therapeutic/prophylactic product being studied. Typically, such events are collected in a standard, systematic format using a graded scale based on functional assessment or magnitude of reaction. This helps to provide a risk profile of the candidate product and a defined listing of expected (or unexpected) adverse events, and whether such events are local or systemic events.

The vaccines described herein may offer good immune protection against multiple (heterologous) strains of ZIKV in addition to the particular ZIKV strain(s) used in production of the vaccine. The ZIKV isolates may exhibit broad neutralizing activity and may cross-neutralize different genotypes/genotypic variants/strains of ZIKV. This occurrence was demonstrated in the murine study described herein, wherein the Puerto Rican vaccine strain protected against challenged by the Brazilian strain.

The purified and inactivated ZIKV vaccine is prepared for administration to mammals, suitably humans, mice, rats or rabbits, by methods known in the art, which can include filtering to sterilize the solution, diluting the solution, adding an adjuvant and stabilizing the solution.

The vaccines disclosed herein may be administered to a human or animal by a number of routes, including but not limited to, for example, parenterally (e.g. intramuscularly, transdermally), intranasally, orally, topically, or other routes know by one skilled in the art. The term parenteral as used hereinafter includes intravenous, subcutaneous, intradermal, intramuscular, intra-arterial injection, or by infusion techniques. The vaccine may be in the form of a single dose preparation or in multi-dose vials which can be used for mass vaccination programs. Suitable methods of preparing and using vaccines can be found in Remington's Pharmaceutical Sciences, Mack Publishing Co., Easton, Pa., Osol (ed.) (1980) and New Trends in Developments in Vaccines, Voller et al. (eds.), University Park Press, Baltimore, Md. (1978), incorporated by reference.

In some embodiments, a vaccine composition as disclosed herein may be administered parenterally in dosage unit formulations containing standard, well-known nontoxic physiologically acceptable adjuvants, and/or vehicles.

In some embodiments, the vaccine compositions may further comprise one or more adjuvants. An "adjuvant" is a substance that serves to enhance, accelerate, or prolong the antigen-specific immune response of an antigen when used in combination with specific vaccine antigens but do not stimulate an immune response when used alone. Suitable adjuvants include inorganic or organic adjuvants. Suitable inorganic adjuvants include, but are not limited to, for example, an aluminum salt, such as aluminum hydroxide gel (alum) or aluminum phosphate, but may also be a salt of calcium (particularly calcium carbonate), iron or zinc, or may be an insoluble suspension of acylated tyrosine, or acylated sugars, cationically or anionically derivitised polysaccharides or polyphospharenes. Other suitable adjuvants are known to one skilled in the art. Suitable Th1 adjuvant systems may also be used, and include, but are not limited to, for example, Monophosphphorly lipid A, other non-toxic derivatives of LPS, and combination of monophosphoryl lipid A, such as 3-de-O-acrylated monophosphorly lipid A (#D-MPL) together with an aluminum salt.

Other suitable examples of adjuvants include, but are not limited to, MF59, MPLA, *Mycobacterium tuberculosis, Bordetella pertussis*, bacterial lipopolysaccharides, aminoalkyl glucosamine phosphate compounds (AGP), or derivatives or analogs thereof, which are available from Corixa (Hamilton, Mont.), and which are described in U.S. Pat. No. 6,113,918; e.g., 2-[(R)-3-Tetradecanoyloxytetradecanoylamino]ethyl, 2-Deoxy-4-O-phosphono-3-O—[(R)-3-tetradecanoyoxytetradecanoy 1]-2-[(R)-3-tetradecanoyoxytetradecanoylamino]-b-D-glucopyra noside, MPL™ (3-O-deacylated monophosphoryl lipid A) (available from Corixa) described in U.S. Pat. No. 4,912,094, synthetic polynucleotides such as oligonucleotides containing a CpG motif (U.S. Pat. No. 6,207,646), COG-ODN (CpG oligodeoxynucleotides), polypeptides, saponins such as Quil A or STIMULON™ QS-21 (Antigenics, Framingham, Mass.), described in U.S. Pat. No. 5,057,540, a pertussis toxin (PT), or an *E. coli* heat-labile toxin (LT), particularly LT-K63, LT-R72, CT-5109, PT-K9/G129; see, e.g., International Patent Publication Nos. WO 93/13302 and WO 92/19265, cholera toxin (either in a wild-type or mutant form). Alternatively, various oil formulations such as stearyl tyrosine (ST, see U.S. Pat. No. 4,258,029), the dipeptide known as MDP, saponin, cholera toxin B subunit (CTB), a heat labile enterotoxin (LT) from *E. coli* (a genetically toxoided mutant LT has been developed), and Emulsomes (Pharmos, LTD., Rehovot, Israel). Various cytokines and lymphokines are suitable for use as adjuvants. One such adjuvant is granulocyte-macrophage colony stimulating factor (GM-CSF), which has a nucleotide sequence as described in U.S. Pat. No. 5,078,996. The cytokine interleukin-12 (IL-12) is another adjuvant which is described in U.S. Pat. No. 5,723,127. Other cytokines or lymphokines have been shown to have immune modulating activity, including, but not limited to, the interleukins 1-alpha (IL-1α), 1-beta (IL-1β), 2 (IL-2), 4 (IL-4), 5 (IL-5), 6 (IL-6), 7 (IL-7), 8 (IL-8), 10 (IL-10), 13 (IL-13), 14 (IL-14), 15 (IL-15), 16 (IL-16), 17 (IL-17) and 18 (IL-18), the interferons-alpha (IFNα), beta (IFN1β) and gamma (IFNγ), granulocyte colony stimulating factor, and the tumor necrosis factors alpha and beta (TNFα and TNFβ respectively), and are suitable for use as adjuvants.

The vaccine compositions can be lyophilized to produce a vaccine against ZIKV in a dried form for ease in transportation and storage. Further, the vaccine may be prepared in the form of a mixed vaccine which contains the inactivated virus described herein and at least one other antigen as long as the added antigen does not interfere with the ability and/or efficacy of the vaccine, and as long as the added antigen does not induce additive or synergistic side effects and/or adverse reactions. The vaccine can be associated with chemical moieties which may improve the vaccine's solubility, absorption, biological half-life, etc. The moieties may alternatively decrease the toxicity of the vaccine, eliminate or attenuate any undesirable side effect of the vaccine, etc. Moieties capable of mediating such effects are disclosed in Remington's Pharmaceutical Sciences (1980) and later editions. Procedures for coupling such moieties to a molecule are well known in the art.

The vaccine may be stored in a sealed vial, ampule or the like. The vaccines disclosed herein can generally be administered in the form of a spray for intranasal administration, or by nose drops, inhalants, swabs on tonsils, or a capsule, liquid, suspension or elixirs for oral administration. In the case where the vaccine is in a dried form, the vaccine is dissolved or suspended in sterilized distilled water before administration.

Vaccine compositions disclosed herein may include an adjuvant. If in a solution or a liquid aerosol suspension, suitable adjuvants can include, but are not limited to, salt solution, sucrose solution, or other pharmaceutically acceptable buffer solutions. Aerosol solutions may further comprise a surfactant.

Among the acceptable vehicles and solvents that may be used include water, Ringer's solution, and isotonic sodium chloride solution, including saline solutions buffered with phosphate, lactate, Tris, and the like. In addition, sterile, fixed oils are conventionally employed as a solvent or suspending medium, including, but not limited to, for example, synthetic mono- or di-glycerides. In addition, fatty acids such as oleic acid find use in the preparation of injectables.

Injectable preparations, for example sterile injectable aqueous or oleaginous suspensions, are formulated according to the known art using suitable dispersing or wetting agents and suspending agents. The sterile injectable preparation are also a sterile injectable solution or suspension in a nontoxic parenterally acceptable diluent or solvent, for example, as a solution in 1,3-butanediol.

Some aspects are illustrated by the following examples. These examples are provided to describe specific embodiments of the technology and do not limit the scope of the disclosure. It will be understood by those skilled in the art that the full scope of the disclosure is defined by the claims appending this specification, and any alterations, modifications, or equivalents of those claims.

EXAMPLES

Example 1. Engineering Non-GMP Lot Production

Figure 2:
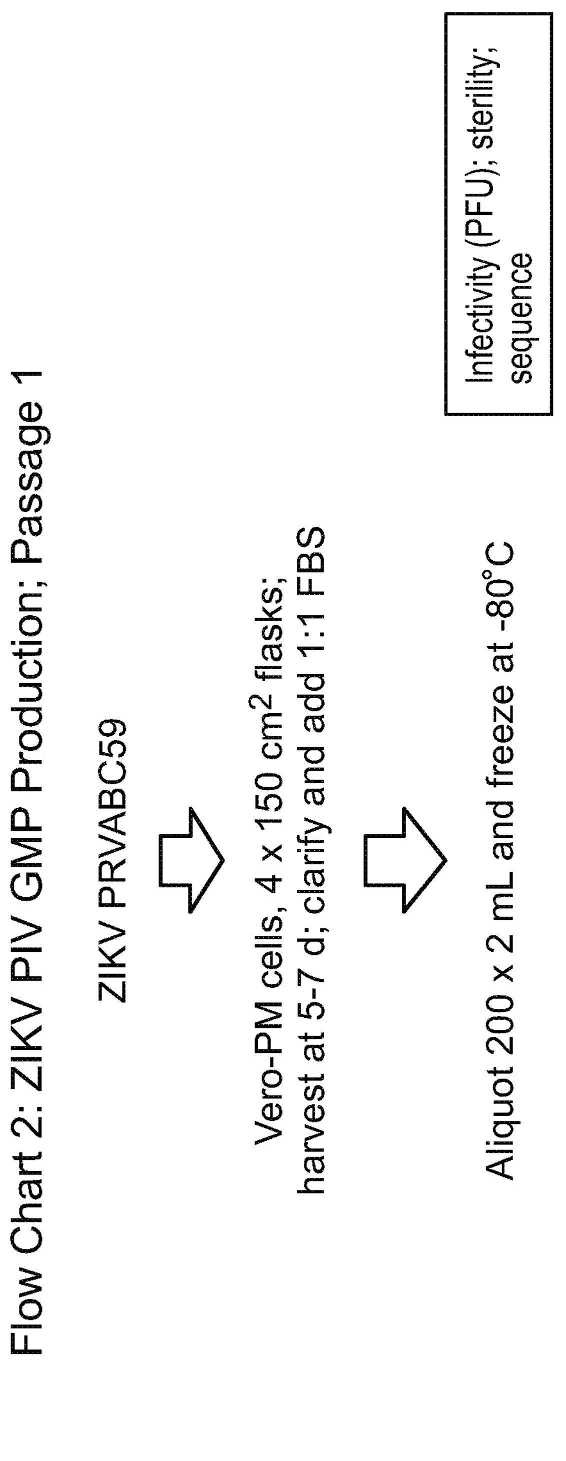
FIG. 2 shows Flow Chart 2 that describes passage 1 of the ZIKV human isolate in Vero cell cultures.
Figure 3:
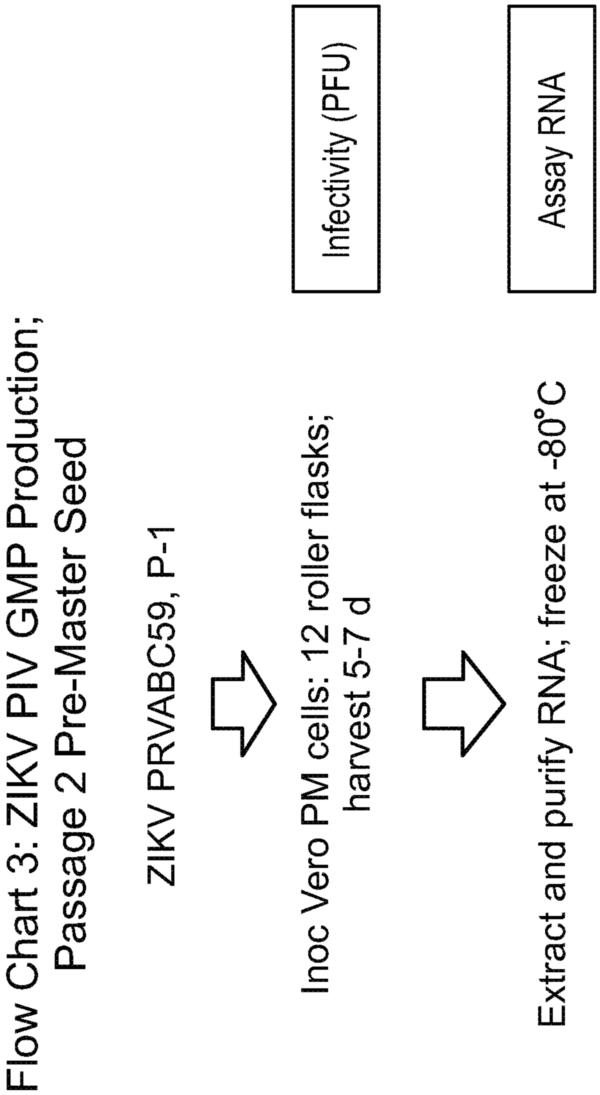
FIG. 3 shows Flow Chart 3 that describes passage of ZIKV in Vero cell cultures using ZIKV passage 1 as inoculum. This passage is also called "pre-master seed".
Figure 4:
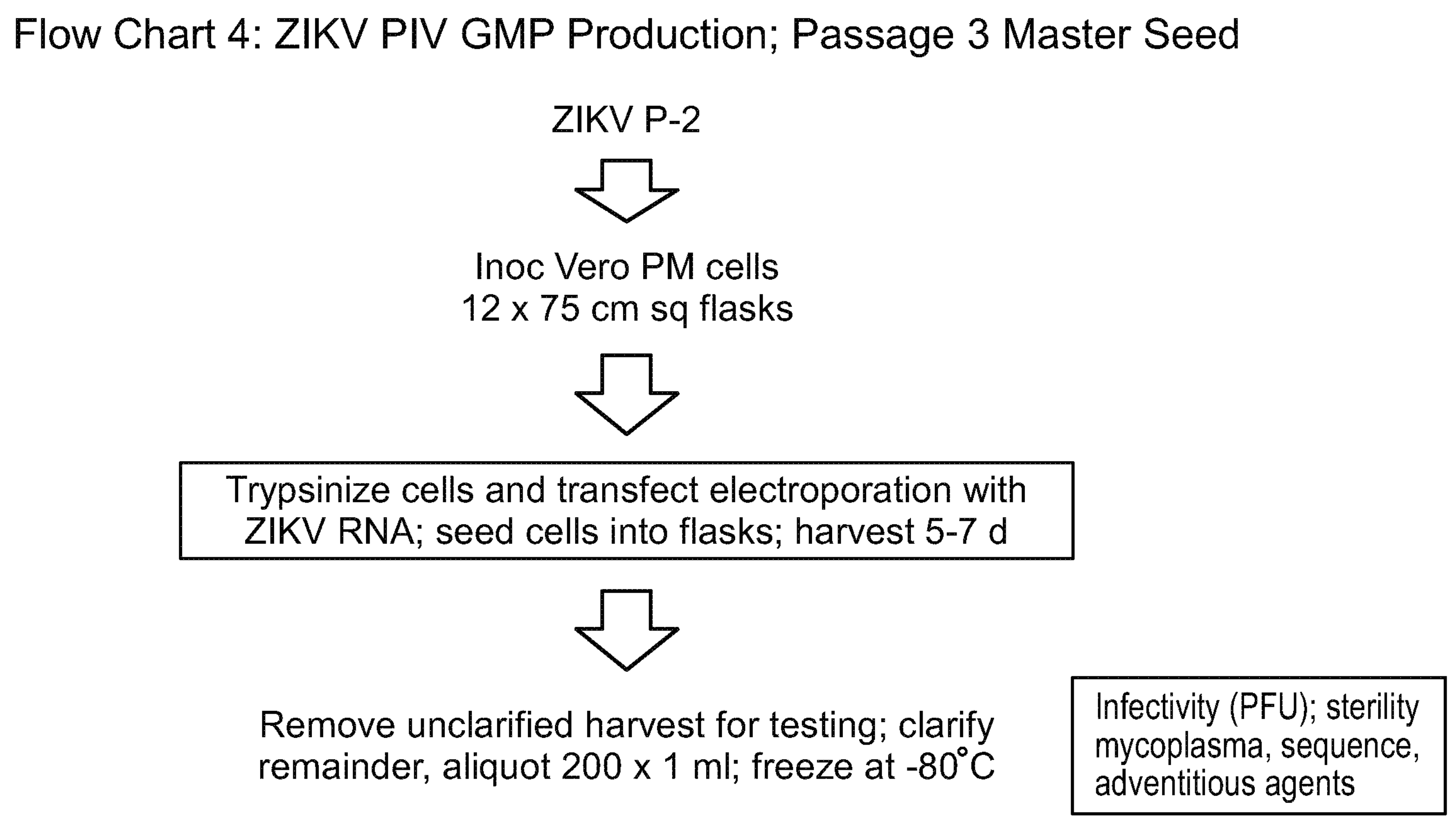
FIG. 4 shows Flow Chart 4 for production of Master Seed passage 3 in Vero cell cultures.
Figure 5:
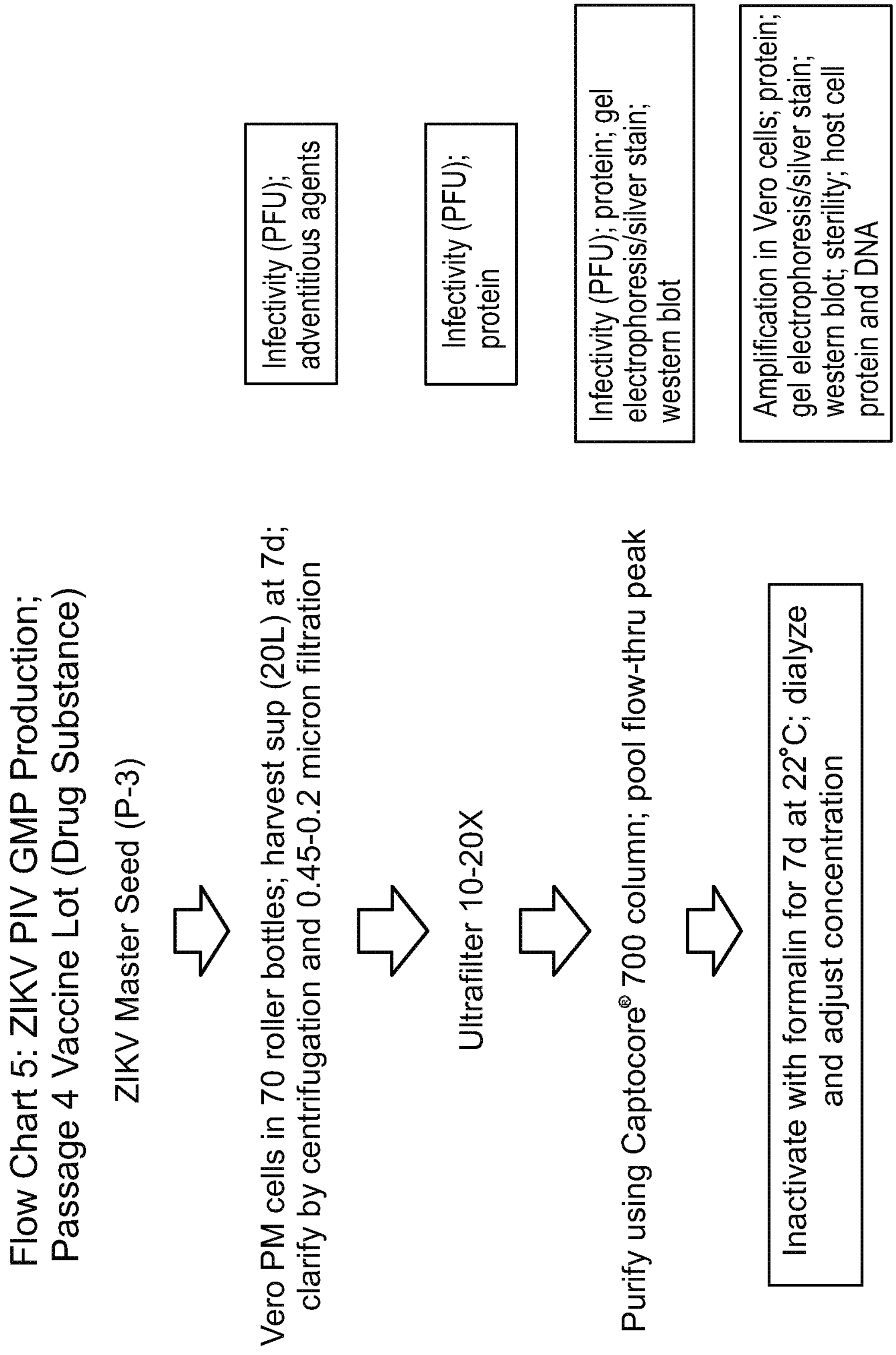
FIG. 5 shows Flow Chart 5, passage 4 in Vero cell cultures for production of a vaccine lot (drug substance).
Figure 6:
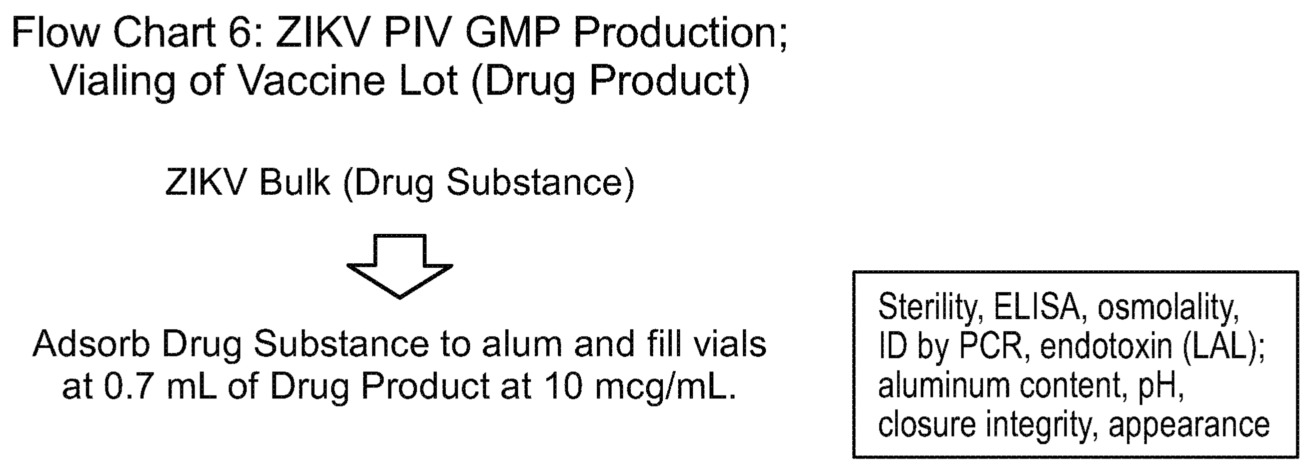
FIG. 6 shows Flow Chart 6 vialing of drug product after adsorption to alum.

FIG. 2 includes Flow Chart 1 with details of the process used to make a purified and inactivated ZIKV. The ZIKV isolate was PRVABC59. The small boxes to the right indicate tests done at each step of the process. The result of this process was the lot that was ultimately used in the mouse studies described below.

Example 2. ZIKV Purified, Inactivated Vaccine GMP Production with PRVABC59

FIGS. 4-7 include Flow Charts 2-5, with details of how ZIKV isolate PRVBC59 is used to make ZIKV vaccine. The small boxes to the right indicate tests done at each step of the process. The passage series is limited to 4 (including the final passage, as part of the purification-inactivation process) to economize time and effort to get the vaccine made. It proved to be a sufficient minimum passage number.

Example 3. Immunizing Dose Identified in Mouse Potency Assay

Animals.

Balb/c, SJL, and C57BL/6 mice were purchased from Jackson Laboratories (Bar Harbor, Me., USA). Mice are vaccinated with 50 μg DNA vaccines by the i.m. (intramuscularly) route or with 1 μg PIV vaccines with alum adjuvant by the i.m. or SQ routes and are then challenged by the i.v. route with $10^5$ viral particles (VP) [$10^2$ plaque-forming units (PFU)] ZIKV-BR]. Immunologic and virologic assays are performed blinded. All animal studies are approved by the BIDMC Institutional Animal Care and Use Committee (IACUC).

PIV Vaccine.

The ZIKV purified inactivated vaccine (PIV) are produced at the Pilot Bioproduction Facility, Walter Reed Army Institute of Research, Silver Spring, Md., USA. The PIV vaccine is based on the Puerto Rican ZIKV PRVABC59 isolate, which was obtained from the Centers for Disease Control and Prevention, Fort Collins, Colo., USA (also available from American Type Culture Collection at ATCC No. VR-1843, Manassas, Va. 20108 USA); the PRVABC59 strain can also be obtained from BEI Resources. The Vero cells used for passage and vaccine production were a derivative of a certified cell line manufactured at The Salk Institute, Swiftwater, Pa. After inoculation, virus is harvested on day 5. Harvested virus is pooled and clarified by centrifugation followed by filtration and ultrafiltration (100,000 molecular weight cutoff). To remove cellular protein and DNA, concentrated virus is treated with benzonase and purified using column chromatography. Column fractions are collected based on optical density associated with viral particles. Positive fractions are pooled, diluted, and formalin was added at a concentration of 0.05% (v/v). After 7 days inactivation at 22° C., formalin is removed by dialysis, and the bulk vaccine is stored at 4° C. Testing prior to use confirmed virus inactivation by PFU assays.

ZIKV Challenge Stocks.

ZIKV stocks were provided by University of Sao Paulo, Brazil (Brazil ZK2015; ZIKV—BR[10]) and the Centers for Disease Control and Prevention, USA (Puerto Rico PRVABC59; ZIKV-PR). Both strains were at passage number 3. Low passage number Vero E6 cells were then infected at an MOI of 0.01 PFU/cell. Supernatant is screened daily for viral titers and harvested at peak growth. Culture supernatants are clarified by centrifugation, and fetal bovine serum was added to 20% final concentration (v/v) and stored at −80° C. The concentration and infectivity of the stocks are determined by RT-PCR (reverse transcriptase polymerase chain reaction) and PFU assays. The viral particle (VP) to plaque-forming unit (PFU) ratio of both stocks is approximately 1,000.

Using a purified inactivated virus (PIV) vaccine derived from the Puerto Rico PRVABC59 strain, groups of Balb/c mice (N=5/group) are administered a single immunization of 1 μg of the PIV vaccine with alum adjuvant or adjuvant alone by the i.m. or s.q. (SQ or s.c.) routes. Antibody titers are substantially higher in the group that received the PIV vaccine by the i.m. route as compared with the SQ route (FIG. 7*a*). At week 4, all mice are challenged with ZIKV-BR by the i.v. route with $10^5$ viral particles (VP) [$10^2$ plaque-forming units (PFU)] of ZIKV-BR.

Figure 7B:
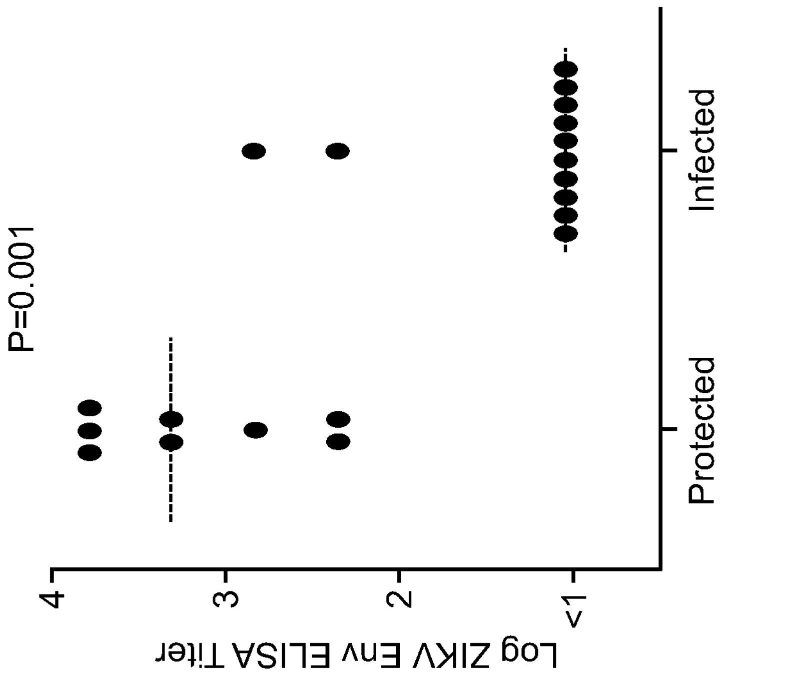
In FIG. 7*b*, correlates of protective efficacy are shown. Gray bars reflect medians. P-value show statistical significance by t-tests. The sham in this experiment is alum. Each dot represents a single mouse, and the gray line is the mean value calculated among all dots.
Figure 8:
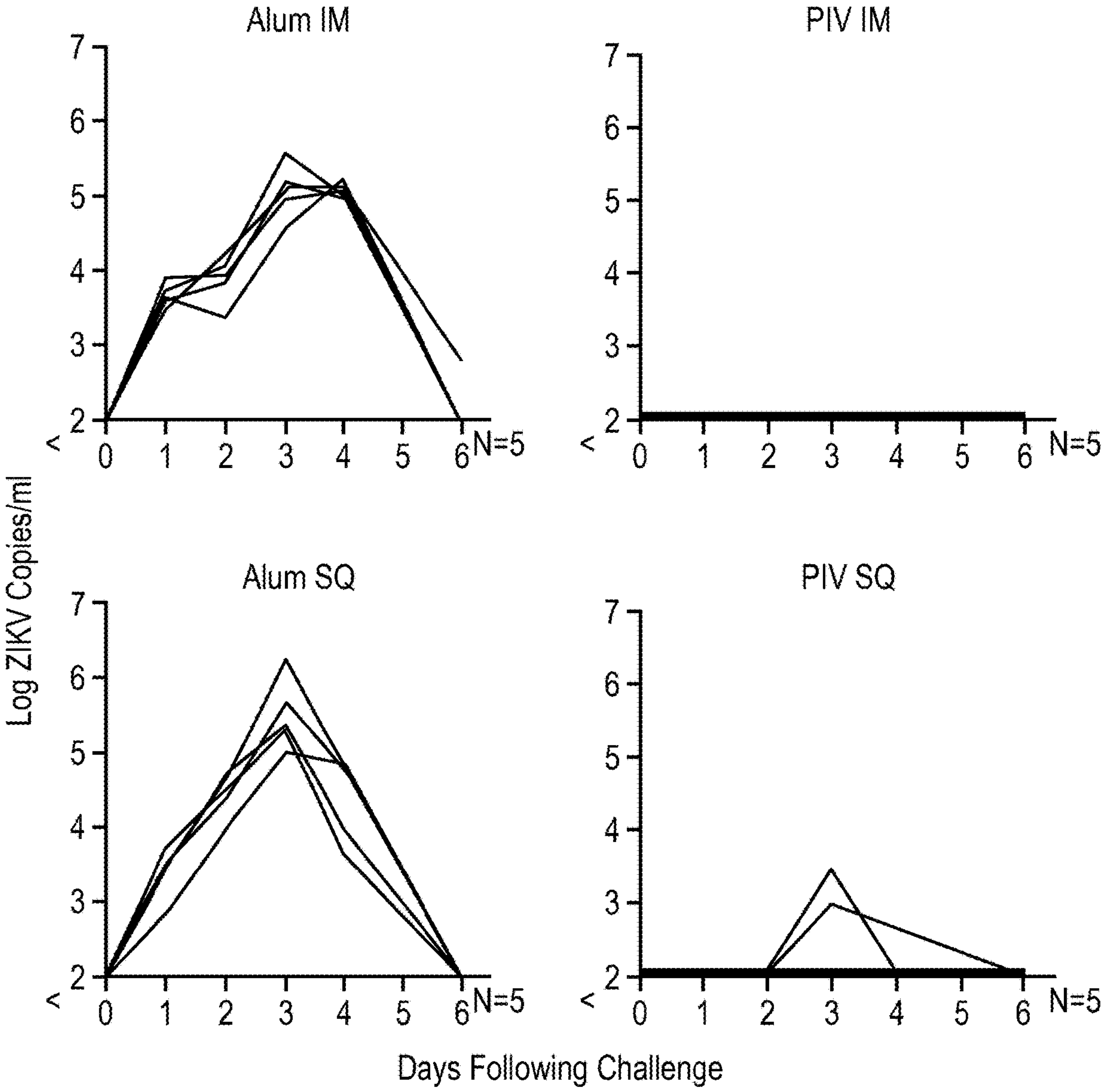
FIG. 8 shows additional results of testing of the purified, inactivated ZIKV vaccine in mice.
Figure 9:
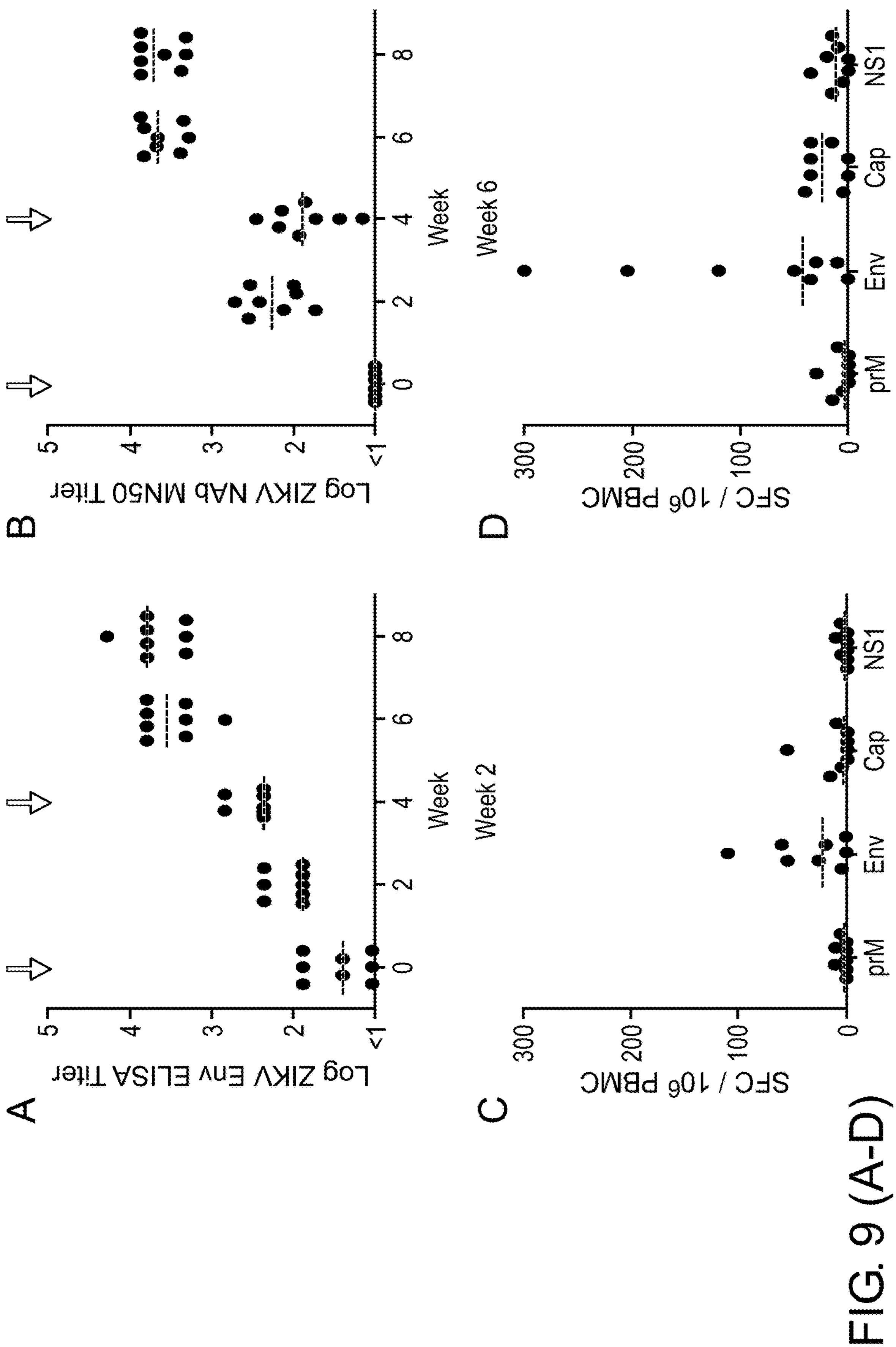
FIG. 9, Panels A-D show the immunogenicity of the ZIKV PIV vaccine in non-human primates.
Figure 10:
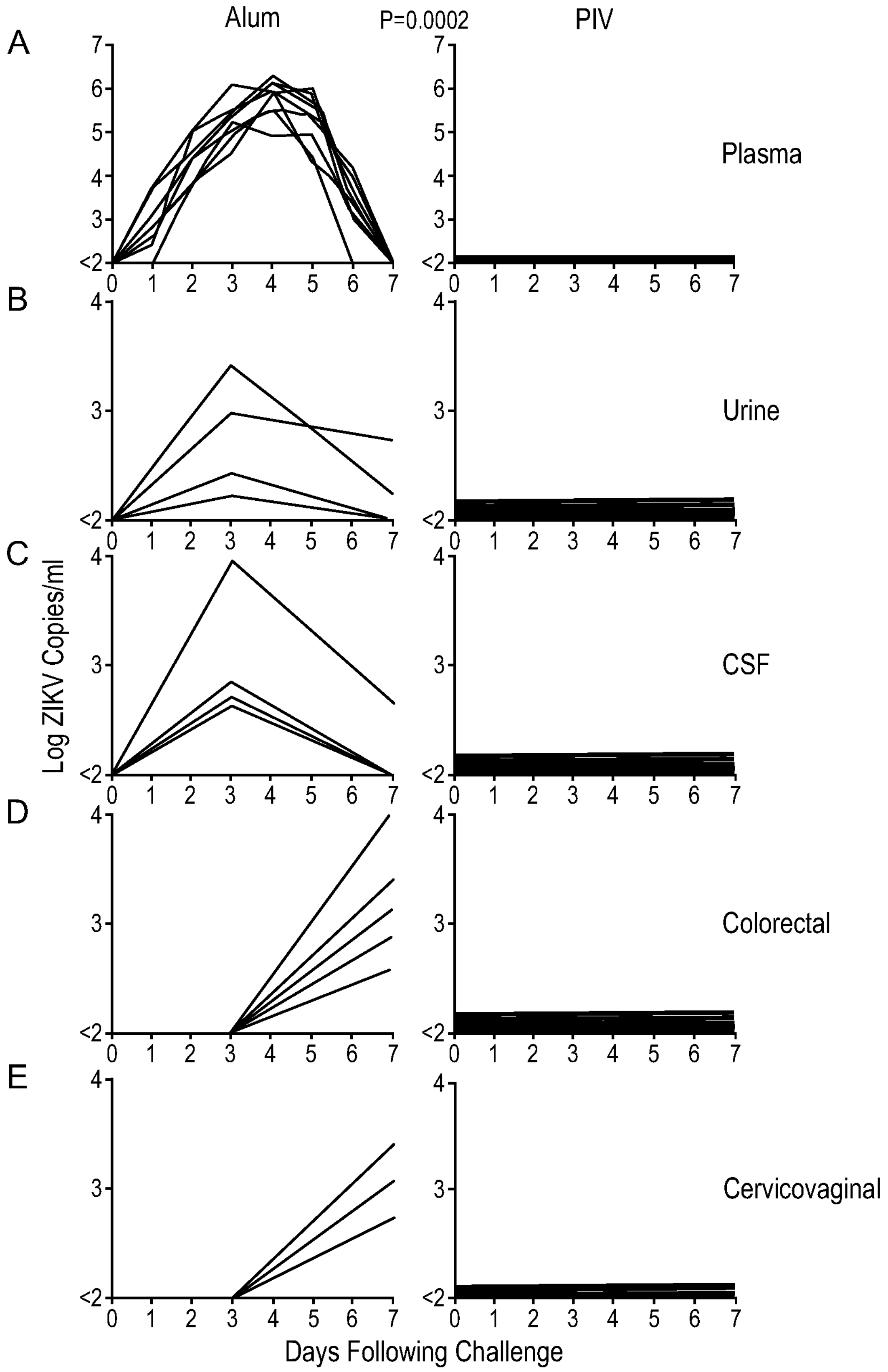
FIG. 10, Panels A-E show protective efficacy of the ZIKV PIV vaccine in non-human primates. PIV vaccinated and sham control rhesus monkeys (N=8/group) were challenged 4 weeks after immunization with 2 doses of ZIKV PiV, by the SQ route using $10^6$ VP ($10^3$ PFU) of ZIKV-BR or ZIKV-PR. Each group contained 6 female and 2 male animals. Viral loads are shown in (FIG. 10A) plasma, (FIG. 10B) urine, (FIG. 10C) CSF, (FIG. 10D) colorectal secretions, and (FIG. 10E) cervicovaginal secretions. Viral loads were determined on days 0, 1, 2, 3, 4, 5, 6, 7 for the plasma samples (FIG. 10A) and on days 0, 3, 7 for the other samples (FIG. 10B-E). Data is shown for all 8 animals in each panel, except for the 6 females for cervicovaginal secretions in (FIG. 10E). P-value shows statistical significance by Fisher's exact test.

Complete protection is observed in the group that received the PIV vaccine by the i.m. route (FIG. 7*b* and FIG. 8). Two mice that received the PIV vaccine by the SQ route show low levels of viremia (FIG. 7), consistent with the lower Env-specific antibody titers in this group (P=0.001, FIG. 7*b*). These data demonstrate that vaccine protection against ZIKV-BR can be achieved in this model with the PIV vaccine that is designed to induce Env-specific antibodies.

The data demonstrate that a single immunization with this PIV vaccine provides complete protection against parenteral ZIKV challenges in mice. Protective efficacy is mediated by vaccine-elicited Env-specific antibodies, as evidenced by statistical analyses of immune correlates of protection (FIG. 7*b*).

Example 4. Protective Efficacy of PIV Against Zika Challenge in Non-Human Primates Having successfully shown protective efficacy of a ZIKV purified inactivated vaccine against ZIKV challenges in mice, we evaluated the immunogenicity and protective efficacy of the PIV in ZIKV challenge studies in rhesus monkeys. Adoptive transfer studies are conducted demonstrating that the ZIKV PIV created antibodies and these antibodies protect against infection.

Materials and Methods

Animals, Vaccines, and Challenges.

Thirty-four (34) outbred, Indian-origin male and female rhesus monkeys (*Macaca mulatta*) were housed at Bioqual, Rockville, Md. Monkeys are immunized by the s.c. route with 5 μg ZIKV purified inactivated virus (PIV) vaccine derived from the PRVABC59 isolate (27) with alum (Alhydrogel; Brenntag Biosector, Denmark) or alum alone at weeks 0 and 4 (N=8/group). Rhesus monkeys are challenged four weeks after the final immunization by the s.c (SQ) route with $10^6$ viral particles (VP) [$10^3$ plaque-forming units (PFU)] ZIKV-BR (Brazil ZKV2015) or ZIKV-PR (PRVABC59) (15).

For adoptive transfer studies, Balb/c mice are infused i.v. with IgG purified from PIV vaccinated monkeys at week 8 and were challenged by the i.v. route with $10^5$ VP ($10^2$ PFU) ZIKV-BR. Rhesus monkeys are infused i.v. with IgG purified from PIV vaccinated monkeys at week 8 and were challenged by the s.c. (SQ) route with $10^6$ VP ($10^3$ PFU) ZIKV-BR. Animals were randomly allocated to groups. Immunologic and virologic assays were performed blinded. All animal studies were approved by the appropriate Institutional Animal Care and Use Committee (IACUC).

RT-PCR.

RT-PCR assays are utilized to monitor viral loads, essentially as previously described (27). RNA is extracted from plasma or other samples with a QIAcube HT (Qiagen, Germany). The wildtype ZIKV BeH815744 Cap gene is utilized as a standard (see GenBank KU365780; Brazil strain; Larocca et al., "Vaccine protection against Zika virus from Brazil," *Nature* 536: 474-478 (Aug. 25, 2016). RNA is purified (Zymo Research, CA, USA), and RNA quality and concentration was assessed by the BIDMC Molecular Core Facility. Log dilutions of the RNA standard are reverse transcribed and included with each RT-PCR assay. Viral loads are calculated as virus particles (VP) per ml and were confirmed by PFU assays. Assay sensitivity was 100 copies/ml.

Pfu Assay.

Vero WHO cells are seeded in a MW6 plate to reach confluency at day 3. Cells are infected with log dilutions of ZIKV for 1 h and overlayed with agar. Cells are stained after 6 days of infection by neutral red staining. Plaques are counted, and titers are calculated by multiplying the number of plaques by the dilution and divided by the infection volume.

ELISA.

Monkey ZIKV Env ELISA kits (Alpha Diagnostic International, TX, USA) are used to determine endpoint binding antibody titers using a modified protocol. 96-well plates coated with ZIKV Env protein were first equilibrated at room temperature with 300 μl of kit working wash buffer for 5 min. 6 μl of monkey serum is added to the top row, and 3-fold serial dilutions are tested in the remaining rows. Samples are incubated at room temperature for 1 h, and plates are washed 4 times. 100 μl of anti-human IgG HRP-conjugate working solution is then added to each well and incubated for 30 min at room temperature. Plates are washed 5 times, developed for 15 min at room temperature with 100 μl of TMB substrate, and the reaction stopped by the addition of 100 μl of stop solution. Plates were analyzed at 450 nm/550 nm on a VersaMax microplate reader using Softmax Pro 6.0 software (Molecular Devices, CA, USA). ELISA endpoint titers are defined as the highest reciprocal serum dilution that yielded an absorbance >2-fold over background values. Log 10 endpoint titers are reported.

Neutralization Assay.

A high-throughput ZIKV microneutralization (MN) assay is utilized for measuring ZIKV-specific neutralizing antibodies, essentially as previously described (27). Briefly, serum samples are serially diluted three-fold in 96-well micro-plates, and 100 μl of ZIKV-PR containing 100 PFU are added to 100 μl of each serum dilution and incubated at 35° C. for 2 h. Supernatants are then transferred to microtiter plates containing confluent Vero cell monolayers (World Health Organization, NICSC-011038011038). After incubation for 4 d, cells are fixed with absolute ethanol:methanol for 1 hour at −20° C. and washed three times with PBS. The pan-flavivirus monoclonal antibody 6B6-C1 conjugated to HRP (6B6-C1 was a gift from J. T. Roehrig, CDC) is then added to each well, incubated at 35° C. for 2 h, and washed with PBS. Plates are washed, developed with 3,3',5,5'-tetramethylbenzidine (TMB) for 50 min at room temperature; the reaction is stopped with 1:25 phosphoric acid, and absorbance is read at 450 nm. For a valid assay, the average absorbance at 450 nm of three non-infected control wells had to be ≤0.5, and virus-only control wells had to be ≥0.9. Normalized absorbance values are calculated, the MN50 titer is determined by a log mid-point linear regression model. The MN50 titer is calculated as the reciprocal of the serum dilution that neutralized ≥50% of ZIKV, and seropositivity is defined as a titer ≥10, with the maximum measurable titer 7,290. Log 10 MN50 titers are reported.

Antibody Peptide Microarrays.

IgG binding to linear peptides spanning ZIKV Env is measured with peptide microarrays (JPT Peptide Technologies, Berlin, Germany), essentially as previously described (29). Briefly, microarrays consisted of 3 identical subarrays containing 153 overlapping 15 amino acid ZIKV Env peptides, which covered 98.2% of available ZIKV Env sequences. Serum is incubated with the microarrays and Alexa Fluor® 647-conjugated anti-human IgG. The readout and image processing was performed with Genepix 4300A scanner/software. Mean fluorescent intensity (MFI) equaled the mean of triplicate peptides and is corrected by subtracting values from matched peptides on control microarrays incubated with secondary antibody alone. The threshold for positivity was >5× noise distribution of the sample size.

ELISPOT.

ZIKV-specific cellular immune responses are assessed by interferon-γ (IFN-γ) ELISPOT assays using pools of overlapping 15-amino-acid peptides covering the prM, Env, Cap, and NS1 proteins (JPT, Berlin, Germany), essentially as previously described (27). 96-well multiscreen plates (Millipore, Mass., USA) are coated overnight with 100 μl/well of 10 μg/ml anti-human IFN-γ (BD Biosciences, CA, USA) in endotoxin-free Dulbecco's PBS (D-PBS). The plates are then washed three times with D-PBS containing 0.25% Tween-20 (D-PBS-Tween), blocked for 2 h with D-PBS containing 5% FBS at 37° C., washed three times with D-PBS-Tween, rinsed with RPMI 1640 containing 10% FBS to remove the Tween 20, and incubated with 2 μg/ml of each peptide and 2×105 monkey PBMC (peripheral blood mononuclear cells) in triplicate in 100 μl reaction mixture volumes. Following an 18 h incubation at 37° C., the plates are washed nine times with PBS-Tween and once with distilled water. The plates are then incubated with 2 μg/ml biotinylated anti-human IFN-γ (BD Biosciences, CA, USA) for 2 h at room temperature, washed six times with PBS-Tween, and incubated for 2 h with a 1:500 dilution of streptavidin-alkaline phosphatase (Southern Biotechnology Associates, AL, USA). Following five washes with PBS-Tween and one with PBS, the plates are developed with nitroblue tetrazolium-5-bromo-4-chloro-3-indolyl-phosphate chromogen (Pierce, Ill., USA), stopped by washing with tap water, air dried, and read using an ELISPOT reader (Cellular Technology Ltd., OH, USA). The numbers of spot-forming cells (SFC) per $10^6$ cells were calculated. The medium background levels were typically <15 SFC per $10^6$ cells.

IgG Purification and Adoptive Transfer.

Polyclonal IgG was purified from plasma from PIV vaccinated monkeys at week 8 using protein G purification kits and pooled (Thermo Fisher Scientific, MA, USA). The purified IgG preparation had a log ELISA titer of 3.30 and a log MN50 titer of 3.30. Purified IgG was infused into groups of naïve recipient Balb/c mice or rhesus monkeys by 5-fold serial dilutions prior to ZIKV-BR (Zika Brazil strain) challenge. Mice received 200, 40, 8, 1.5, or 0 μl of the IgG preparation. Monkeys received 10, 2, or 0 ml of the IgG preparation.

Statistical Analyses.

Analysis of virologic and immunologic data is performed using GraphPad Prism v6.03 (GraphPad Software, CA, USA). Comparisons of groups are performed using t-tests and Wilcoxon rank-sum tests. Correlations are assessed by Spearman rank-correlation tests.

Vaccine Study in Rhesus Monkeys.

Figure 13:
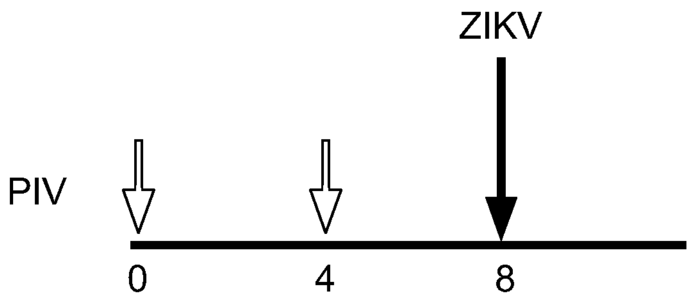
FIG. 13 shows PIV vaccine schedules for the non-human primates. Immunization and challenge schedules for the ZIKV purified inactivated virus (PIV) vaccine. Gray arrows indicate vaccinations, and black arrows indicate ZIKV challenges. The numbers reflect study weeks. Notably, this schedule is contemplated for human use as well. The data generated, along with what is already known about PIV for flaviviruses, is reasonably demonstrative of what will be safe and effective in humans.
Figure 14:
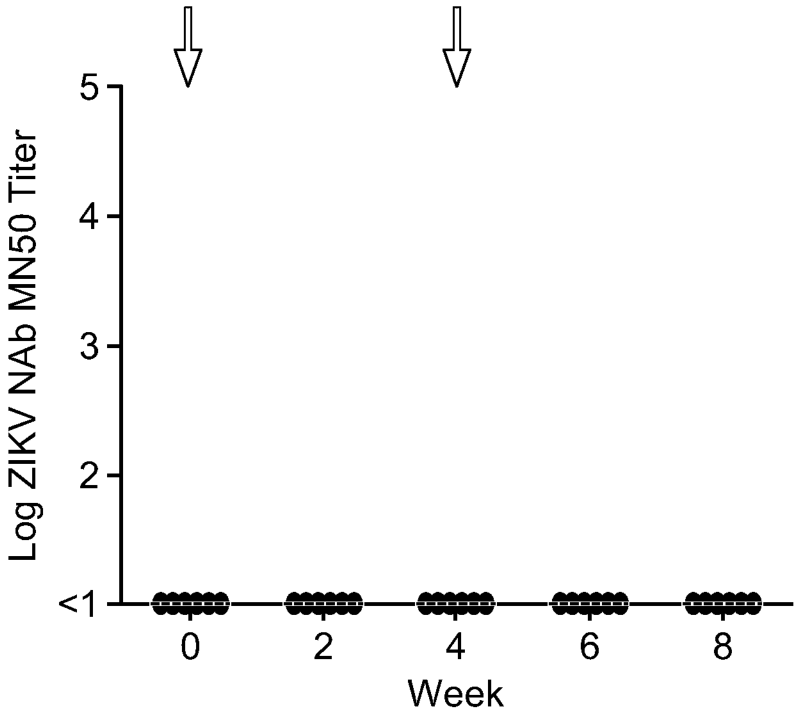
FIG. 14 shows MN50 titers in the sham controls in the ZIKV PIV vaccine study for non-human primates. ZIKV-specific microneutralization (MN50) titers following immunization of rhesus monkeys with sham (alum only) at weeks 0 and 4 (gray arrows). Gray bars reflect medians.
Figure 15:
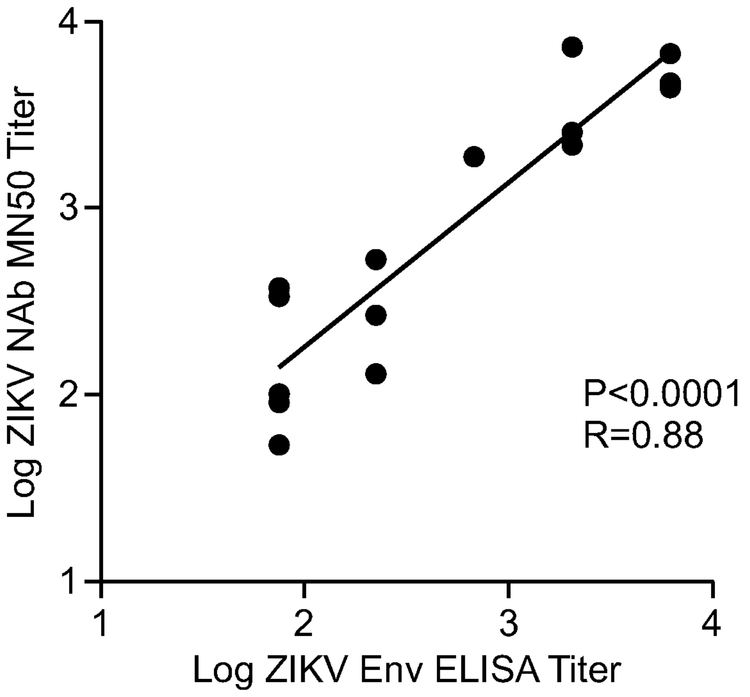
FIG. 15 shows correlation of binding and neutralizing antibody titers in the ZIKV PIV vaccine study for non-human primates. Correlations of binding ELISA titers and microneutralization (MN50) titers at weeks 2 and 6 are combined from the ZIKV PIV vaccine study. P-value reflects a Spearman rank-correlation test.
Figure 16:
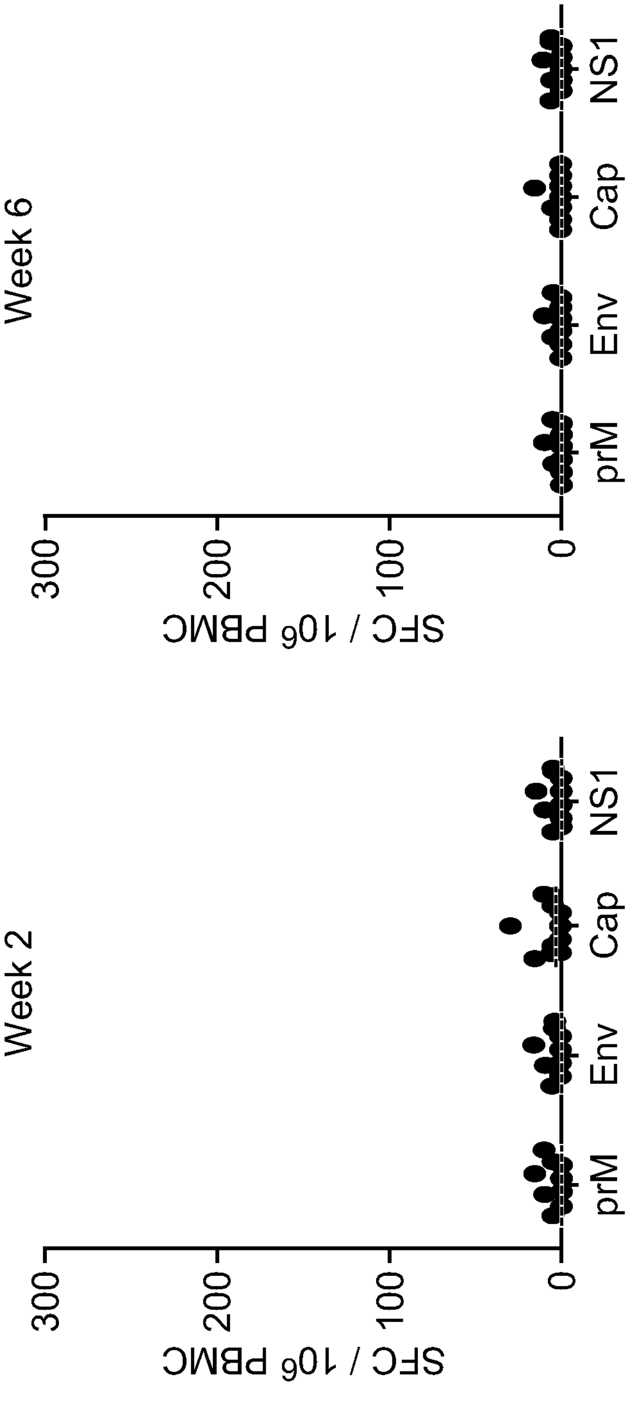
FIG. 16 shows IFN-γ ELISPOT assays in the sham controls in the ZIKV PIV vaccine study in non-human primates. Cellular immune responses are measured by IFN-γ ELISPOT assays to prM, Env, Cap, and NS1 at week 2 and week 6 following immunization of rhesus monkeys. Gray bars reflect medians.

Sixteen rhesus monkeys are immunized by the subcutaneous route with 5 μg ZIKV PIV vaccine with alum (N=8) or sham vaccine (alum only) (N=8) at weeks 0 and 4 (FIG. 13). All PIV vaccinated animals developed ZIKV Env-specific binding antibodies by ELISA as well as ZIKV-specific neutralizing antibodies by microneutralization (MN50) assays at week 2 following initial immunization. Median log antibody titers at week 2 are 1.87 by ELISA (FIG. 9A) and 2.27 by MN50 assays (FIG. 9B). Following the week 4 boost immunization, median log antibody titers increased substantially to 3.54 by ELISA (FIG. 9A) and 3.66 by MN50 assays (FIG. 9B) at week 6. In contrast, sham control monkeys did not develop detectable ZIKV-specific antibody responses (FIG. 14). Binding antibody titers correlated with neutralizing antibody titers in the PIV vaccinated animals (P<0.0001, R=0.88, Spearman rank correlation test; FIG. 15), although only minimal antibody-dependent cellular phagocytosis responses were observed. The majority of PIV vaccinated monkeys (FIGS. 9C-D), but not sham control animals (FIG. 16), also developed modest cellular immune responses, primarily to Env, as measured by interferon (IFN)-γ ELISPOT assays.

Figure 17:
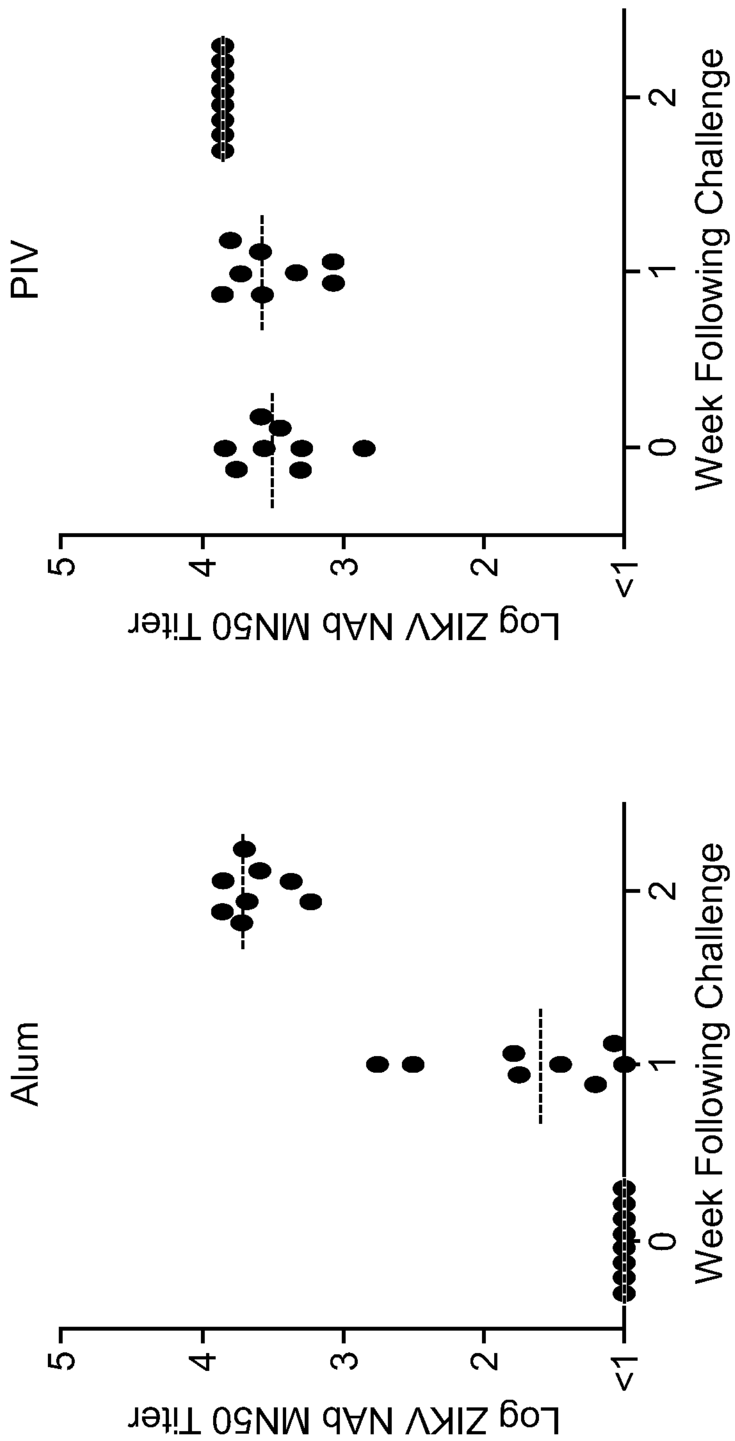
FIG. 17 show MN50 titers following ZIKV challenge in the ZIKV PIV vaccine study for non-human primates. ZIKV-specific microneutralization (MN50) titers following ZIKV-BR challenge in rhesus monkeys that received the ZIKV PIV vaccine or sham (alum only). The maximum measurable log MN50 titer in this assay was 3.86. Gray bars are medians.
Figure 18:
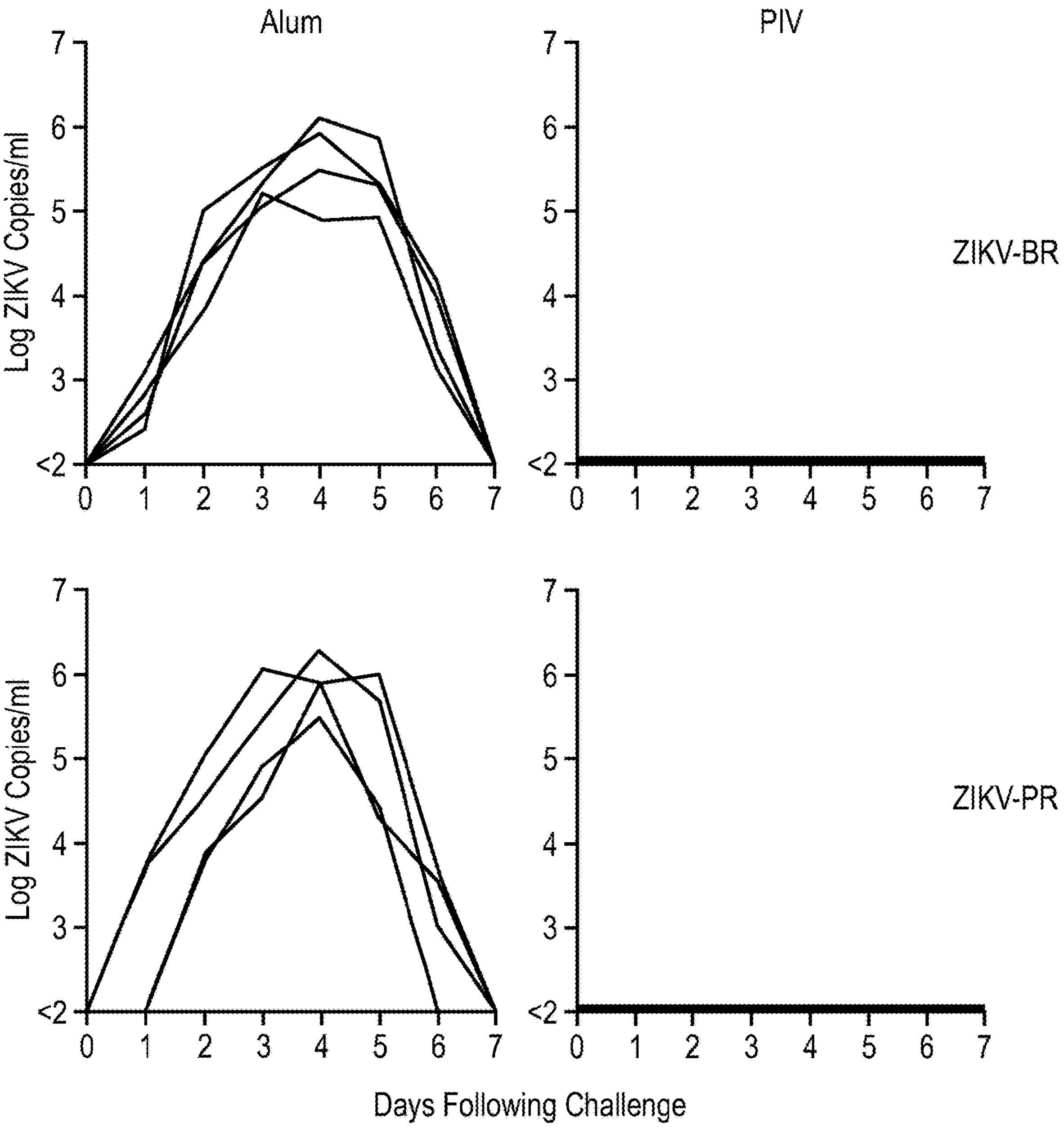
FIG. 18 shows viral loads in the ZIKV PIV vaccine study in non-human primates. Plasma viral loads in PIV vaccinated monkeys and sham controls following challenge with ZIKV-BR or ZIKV-PR (N=4/group).
Figure 19:
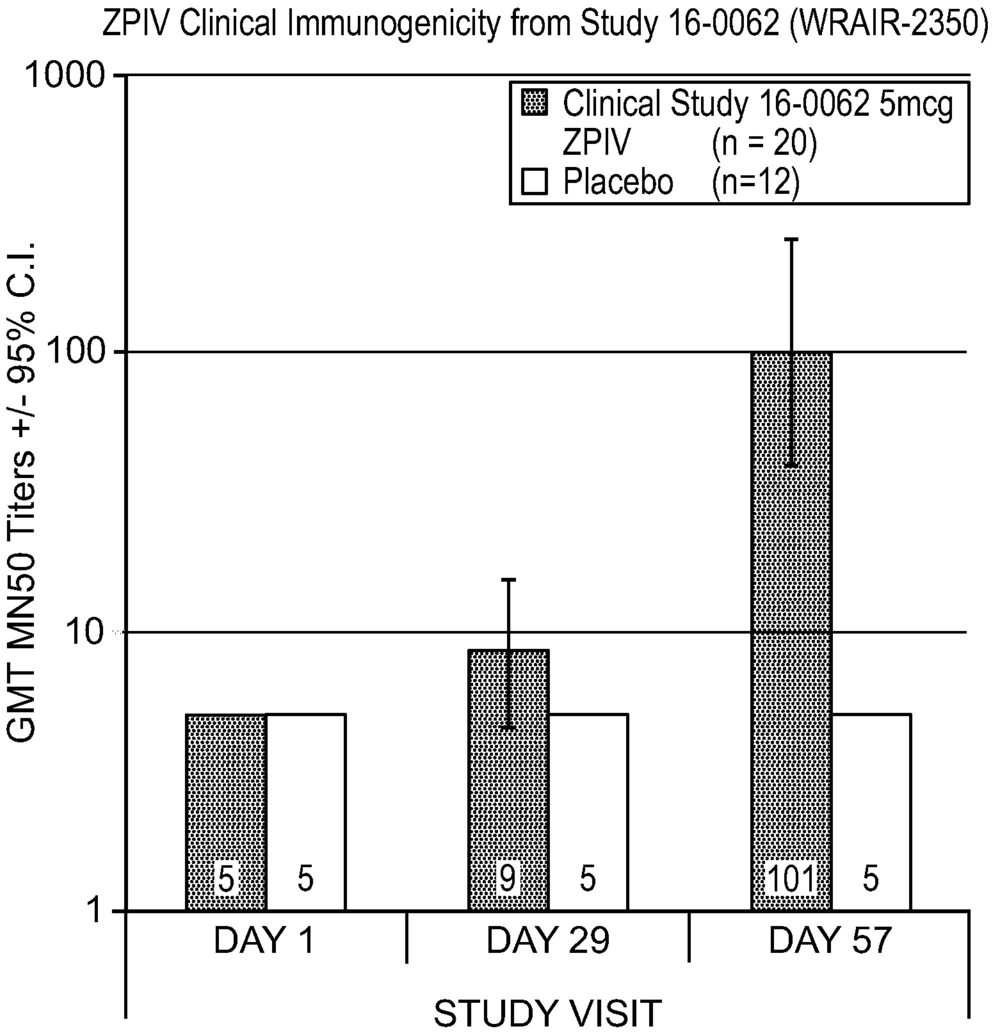
FIG. 19 shows results of a human clinical trial of ZIKV PIV. The bars represent geometric mean neutralizing (MN50) titers and 95% confidence intervals for volunteers following one and two doses of ZIKV PIV.
Figure 20:
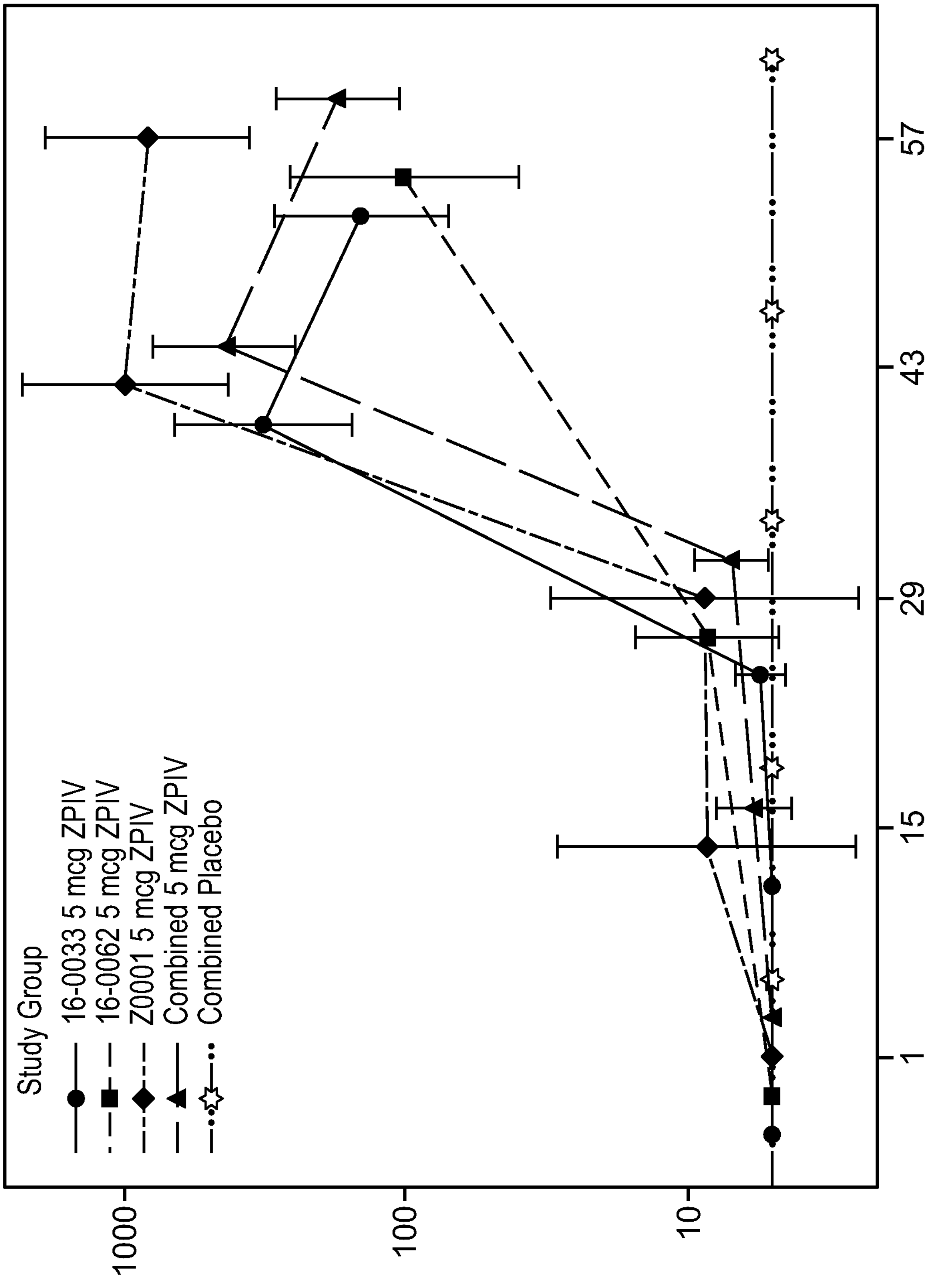
FIG. 20 depicts the geometric mean antibody titers determined by MN 50 assay based on the trial study site in human volunteers.
Figure 21:
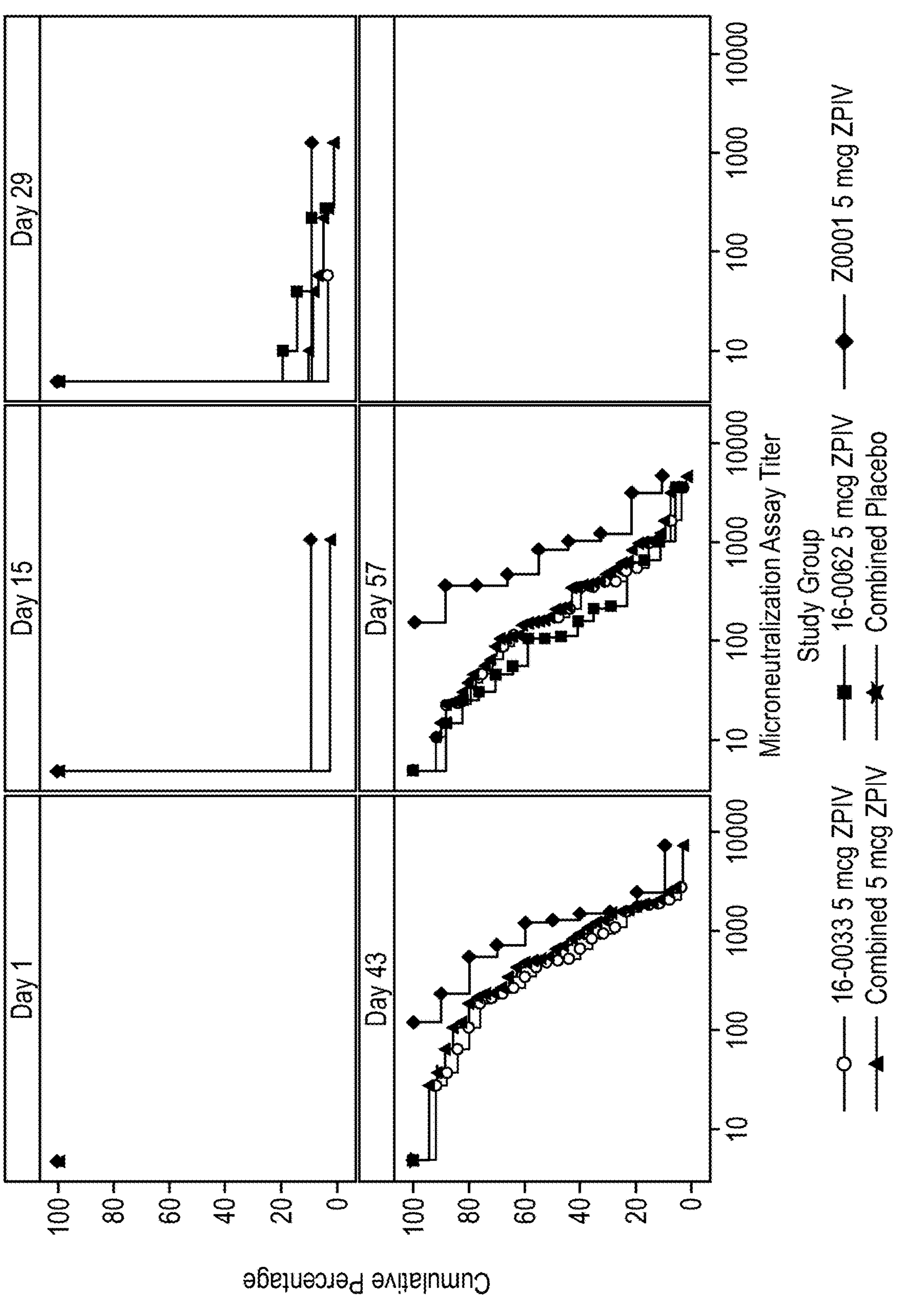
FIG. 21 depicts the reverse cumulative curve of neutralizing antibody titers depicting the study site and the study day on which the titer was measured. The curves are informative, because they provide a comprehensive look at the antibody titers for the entire cohort at a point in time. For example, at day 57 more than 40% of the cohort (y axis) have a titer above 100 (x axis). Approximately 10% of the cohort has titers of 1000 at this same time point. It is evident that although the Trial Study Site 2 and Trial Study Site 1 have very similar curves; trial study site 3 appears to be an outlier with a higher percentage of the cohort having higher titers.

To assess the protective efficacy of the PIV vaccine against ZIKV challenge, we infected PIV immunized and sham control monkeys by the subcutaneous route with $10^6$ viral particles (VP) [$10^3$ plaque-forming units (PFU)] of ZIKV-BR or ZIKV-PR (N=4/group) (27). Viral loads following ZIKV challenge are quantitated by RT-PCR (27), and viral infectivity is confirmed by growth in Vero cells. ZIKV-specific MN50 titers increased following challenge, particularly in the sham controls (FIG. 17). Sham control monkeys exhibited 6-7 days of detectable viremia with median peak viral loads of 5.82 log copies/ml (range 5.21-6.29 log copies/ml; N=8) on day 3-5 following challenge (FIG. 10A). Virus was also detected in the majority of sham control animals in urine and cerebrospinal fluid (CSF) on day 3, as well as in colorectal secretions and cervicovaginal secretions on day 7 (FIG. 10B-E). In contrast, PIV vaccinated monkeys show complete protection against ZIKV challenge, as evidenced by no detectable virus (<100 copies/ml) in blood, urine, CSF, colorectal secretions, and cervicovaginal secretions in all animals following challenge (N=8; P=0.0002, Fisher's exact test comparing PIV vaccinated animals vs. sham controls). We were unable to assess ZIKV in semen in the male animals in this study due to inadequate sample volumes. No major differences in plasma viral loads were observed between the sham controls that received ZIKV-BR vs. ZIKV-PR (FIG. 18).

In this study, we demonstrated that our PIV platform provided complete protection against ZIKV challenge in rhesus monkeys. No specific clinical safety adverse effects related to the vaccine were observed. The protective efficacy of this ZIKV PIV vaccine in mice is described above (27). The present data confirm and extend these prior studies by demonstrating robust protection with these vaccines against ZIKV challenge in nonhuman primates, and specifically utilizing the dose, route, and schedule of these vaccines that are typically evaluated in clinical trials.

Adoptive Transfer Studies in Mice and Non-Human Primates.

The mechanism of the observed protection by adoptive transfer studies was explored. IgG is purified from plasma from ZIKV PIV vaccinated monkeys at week 8 by protein G affinity chromatography. Vaccine-elicited, ZIKV-specific IgG is then infused into four groups of naïve Balb/c mice (N=5/group) by 5-fold serial dilutions of the purified IgG preparation, which had a log ELISA titer of 3.30 and a log MN50 titer of 3.30. Following infusion, these groups of recipient mice (designated I, II, III, IV) had median log ELISA titers of 2.83, 2.35, 1.40, and <1.00 (FIG. 11A) and median log MN50 titers of 2.93, 1.77, 1.14, and <1.00 (FIG. 11B). Mice are then challenged by the intravenous route with $10^5$ VP ($10^2$ PFU) of ZIKV-BR, as previously described (27). The higher two doses of purified IgG provides complete protection following ZIKV challenge, whereas the lower two doses of purified IgG results in reduced viremia as compared with sham infused control mice (FIG. 11C-E).

Vaccine-elicited, ZIKV-specific IgG was also infused into two groups of naïve rhesus monkeys (N=2/group). Following infusion, these groups of recipient monkeys (designated I, II) had median log MN50 titers of 2.11 and 1.22 (FIG. 12A). Monkeys are then challenged with $10^6$ VP ($10^3$ PFU) of ZIKV-BR. In the animals that received the higher IgG dose, one animal is completely protected and the other showed a blip of viremia on days 3-5 (FIG. 12B). No enhancement of viral replication was observed at subtherapeutic IgG concentrations. Taken together, these data demonstrate that purified IgG from ZIKV PIV vaccinated rhesus monkeys provided passive protection following adoptive transfer in both rodents and primates. Therefore, the PIV ZIKV produced from the Puerto Rican strain (PRVABC59) is capable of producing ZIKV-specific neutralizing antibodies and completely protected monkeys against ZIKV strains from both Brazil and Puerto Rico.

Figure 11:
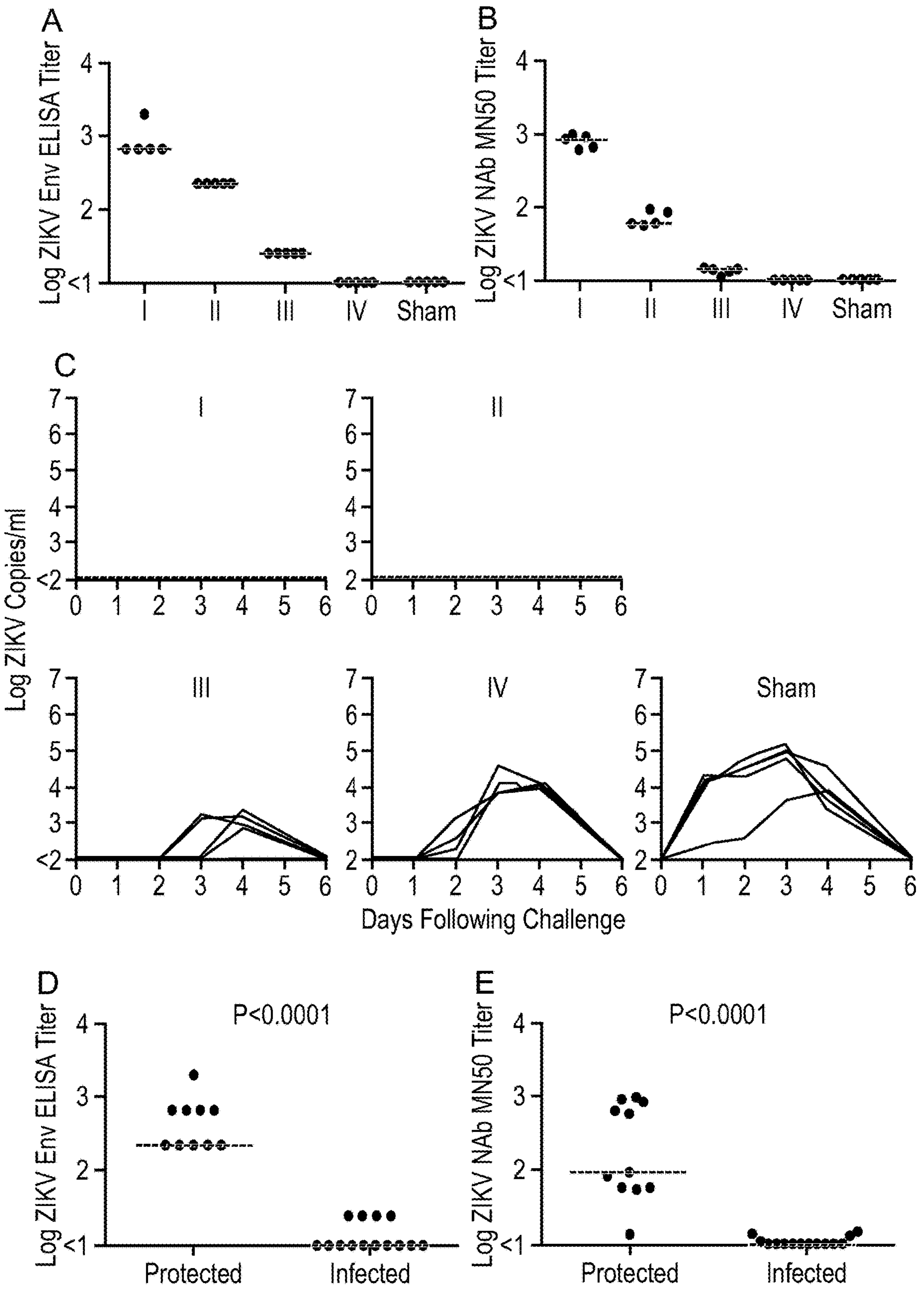
FIG. 11, Panels A-E show data from adoptive transfer studies in mice.
Figure 12:
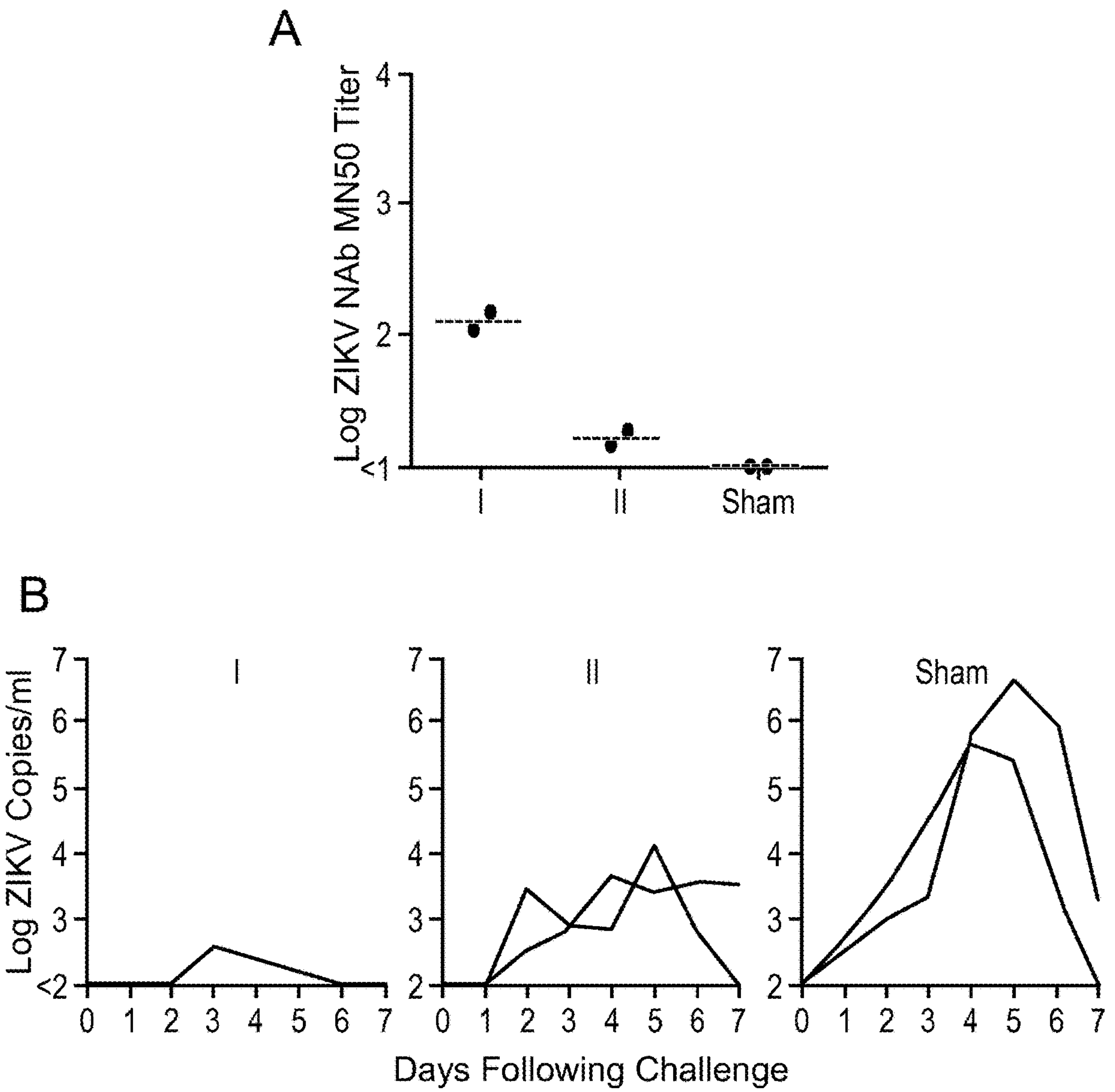
FIG. 12, Panels A-B show adoptive transfer studies in rhesus monkeys.

The adoptive transfer studies demonstrate that vaccine-elicited antibodies are sufficient for protection against ZIKV challenge. Moreover, passive protection in mice and rhesus monkeys is observed at relatively low antibody titers (FIGS. 11, 12). Such antibody titers are likely achievable by these vaccine platforms in humans, thus raising optimism for the development of a ZIKV vaccine for humans. Notably, this can have implication for impact of cross-reactive antibodies against dengue virus and other flaviviruses. Secondary infection with a heterologous dengue serotype can be clinically more severe than initial infection, which may or may not reflect antibody-dependent enhancement (30, 31). Cross-reactive antibodies between ZIKV and dengue virus have also been described (32, 33), and dengue-specific antibodies have been reported to increase ZIKV replication in vitro (34).

The consistent and robust antibody-based correlates of vaccine protection against ZIKV challenge in both rodents and primates suggest the generalizability of these findings. The mouse and primate data track each other well, and yield the same conclusions: Zika PIV generates robust antibodies to Zika, and those antibodies protect both species against Zika infection. Similar correlates of protection, and specifically neutralizing antibody titers >10, have been reported for other flavivirus vaccines in humans (35-37). Taken together, these data are reasonably predictive for how ZIKV vaccines will perform in humans. PIV vaccines have been evaluated previously in clinical trials for other flaviviruses, including dengue virus, tick-borne encephalitis virus, and Japanese encephalitis virus (38-42).

The production process described herein is suitable for further development and production of an inactivated ZIKV vaccine.

Comparison of the PIV vaccine for Zika virus with an adenovirus vector based vaccine was also performed. The ZIKV pre-membrane (prM) and Env proteins with the signal peptide deleted for enhanced expression (prM-Env amino acids 216-794; also known as M-Env), adenovirus (Ad) vectors expressing this immunogen and purified PIV vaccines were compared. All three types of vaccines are shown to induce ZIKV-specific neutralizing antibodies and protected both mice and rhesus monkeys against challenge with ZIKV strains from Brazil and Puerto Rico. Abbink et al., "Protective efficacy of multiple vaccine platforms against Zika virus challenged in rhesus monkeys," *Science* 353: 1129-32 (2016) and D. H. Barouch et al., "Prospects for a Zika Virus Vaccine," Immunity 46: 176-182 (2017); and Larocca et al., "Vaccine protection against Zika virus from Brazil," *Nature* 536: 474-478. In rhesus monkeys, the ZIKV PIV vaccine disclosed herein and the Ad vector-based vaccine both induced neutralizing antibodies after a single immunization and proved more immunogenic than the DNA vaccine. The DNA vaccine did provide sufficient neutralizing antibodies only after two immunizations, which is a less preferred method of immunizing subjects when trying to reduce a viral outbreak. D. H. Barouch et al. (2017).

Example 5. ZIKV PIV Performance in Human Trials

Five trials constitute the phase 1 clinical development program for ZPIV and were designed to explore different the safety and immunogenicity performance across a variety of potential use scenarios.

Trial 1

ZIKV PIV (ZPIV) is provided to individuals with or without previous exposure to yellow fever and Japanese encephalitis vaccines to assess safety and immunogenicity of ZPIV in scenarios where people will have pre-existing immunity to these flaviviruses through vaccination; these data could also be reasonably extrapolated to natural exposures as well Trial 2

ZPIV is explored across a range of antigen doses in an attempt to define the optimal dose of antigen as well as lower limits of antigen concentration required to effectively immunize a recipient Trial 3

ZPIV is explored across a range of schedules in an attempt to define the optimal dosing schedule to effectively immunize a recipient and the potential requirement for booster doses to create durable immune responses Trial 4

ZPIV will be administered in an area in Puerto Rico with a high rate of dengue virus priming as well as an areas having recently experienced a large Zika outbreak to understand safety and immunogencity performance in scenarios where dengue and Zika are potentially endemic.

Trial 5

ZPIV will be administered in sequential, heterologous prime boost scenarios with the NIH DNA vaccine candidate to understand safety and potentially advantageous immunogenicity performance characteristics Data was reviewed for the ZPIV recipients without known previous exposure through natural infection or vaccination to Zika or other flaviviruses. Two doses were administered at 0 and 28 days, 5 μg per dose, and adjuvanted with alum. Safety and immunogenicity data were collected out to day 57. A total of 67 individuals were in this group, with 55 receiving ZPIV and 12 receiving placebo. Volunteers represent enrollment from Trial Groups 2, 1 and 3 respectively.

A relatively equal number of male and female volunteers were enrolled; 52 and 48%, respectively. The preponderance of volunteers were white (71%) or black (19%). The mean age was 31.5 years with a decline in the mean age from Trial Group 2 (33.3) to Trial Group 1 (30.9) to Trial Group 3 (27.9).

There were no deaths, serious adverse events related to vaccination, or dis-enrollments related to an adverse event. There were no severe local adverse events (pain, redness, swelling at the site of injection). Most local adverse events were infrequent in occurrence and mild in severity. Pain and tenderness at the injection site occurred more frequently and were overwhelmingly mild in severity. Any systemic sign or symptom was reported in a majority of enrolled volunteers with the majority being mild (49.2%) and a smaller proportion being graded as moderate (14.9%) or severe (1.5%). A single (1.5%) volunteer reported nausea and/or vomiting; there were no other severe systemic signs or symptoms. In summary, despite not knowing which local or systemic signs or symptoms were reported by placebo or vaccine recipients, the safety profile in these 67 volunteers is acceptable, comparable to many currently licensed vaccines, and supports advancing clinical development.

Immunogenicity data was generated through the use of microneutralization assay and the titers reported indicating the readout representing the titer at which 50% of the control virus is neutralized (MN50). The cutoff for determining a vaccine take (seroconversion) is a MN titer of 1:10. Titers are measured—28 days following the second dose of vaccine (study day 57). The MN50 titer found to be protective in mice and non-human primate studies ranges from 1:10-1:100, respectively. For context, the neutralizing antibody titers accepted by the regulatory agencies as correlates or surrogates of protection for licensed flavivirus vaccines against yellow fever, Japanese encephalitis (JE), and tick borne encephalitis ranges from 1:5-1:10.

Seroconversion measured by the MN50 assay, >1:10 titer, at study day 57 was 92% across the Trial 2 Group, Trial 3 Group, and Trial 1 Group study sites with a range of site specific seroconversion rates of Trial 2 Group 92%, Trial 1 Group 88%, and Trial 3 Group 100%. Seroconversion with a titer cutoff of 1:100 (protective titer in non-human primates) was Trial Group 2 65%, Trial Group 1 59%, and Trial Group 3 100%; overall rate of 69%. Antibody kinetics based on MN50 titers indicating a slight rise in antibody after the first dose of vaccine with mean titers remaining below the 1:10 titer cutoff and then a robust and brisk rise in antibody titer for the Trial Group 2 and Trial Group 3 volunteers following dose two. Peak titers for Trial Group 1 and Trial Group 3 volunteers occur on or about study day 43 (2 weeks post dose two) and are between 500 and 1000. There is a gradual decline in titer between day 43 and day 57 with the final data point indicating titers between ~200-900. The Trial Group 1 volunteers have a distinct kinetic curve following dose two with a gradual rise and no decline in titer peaking at ~100 at day 57.

Detailed antibody data are provided in the table below representing site specific geometric mean titers and the confidence interval around these titers based on the day of collection and the study site where the collection occurred. Peak titers are also represented.

| | | 5 mcg ZPIV | | | | Placebo |
|---|---|---|---|---|---|---|
| Time Point[a] | Statistic | 16-0033 (N = 25) | 16-0062 (N = 20) | Z0001 (N = 10) | All (N = 55) | All (N = 12) |
| Day 1 | N* | 25 | 20 | 10 | 55 | 12 |
| | GMT | 5.0 | 5.0 | 5.0 | 5.0 | 5.0 |
| | 95% CI | — | — | — | — | — |
| Day 15 | N* | 25 | — | 10 | 35 | 7 |
| | GMT | 5.0 | — | 8.6 | 5.8 | 5.0 |
| | 95% CI | — | — | 2.5, 28.8 | 4.3, 8.0 | — |
| Day 29 | N* | 25 | 20 | 10 | 55 | 12 |
| | GMT | 5.5 | 8.5 | 8.7 | 7.0 | 5.0 |
| | 95% CI | 4.5, 6.8 | 4.7, 15.3 | 2.5, 30.4 | 5.2, 9.5 | — |
| Day 43 | N* | 25 | — | 10 | 35 | 7 |
| | GMT | 316.9 | — | 983.3 | 437.9 | 5.0 |
| | 95% CI | 152.9, 656.6 | — | 425.4, 2272.5 | 245.7, 780.6 | — |
| Day 57 | N* | 25 | 17 | 9 | 51 | 12 |
| | GMT | 142.9 | 100.8 | 820.6 | 173.1 | 5.0 |
| | 95% CI | 70.3, 290.4 | 39.7, 255.7 | 357.1, 1885.8 | 104.6, 286.5 | — |
| Peak Titer | N* | 25 | 20 | 10 | 55 | 12 |
| | GMT | 345.6 | 64.2 | 1061.7 | 229.8 | 5.0 |
| | 95% CI | 166.4, 718.0 | 25.3, 163.2 | 452.8, 2489.2 | 132.6, 398.4 | — |

Based on the disclosure and the above data the compositions including inactivated ZIKV demonstrate that the compositions are immunogenic and that vaccines comprising inactivated ZIKV are protective against infection with ZIKV.

The available immunogenicity data for the ZPIV indicates the candidate is moderate to highly immunogenic following two doses measured out to study day 57. When aggregated across the sites, titers in the majority of the vaccinated population exceed what is believed to a protective titer based on pre-clinical animal studies. To further support this contention, BIDMC completed a passive transfer study using purified antibody collected from the sera of human vaccine recipients. Nine (9) animals were fully protected by the human antibody following challenge, 1 was partially protected, and 2 were not protected; these data track with the randomization scheme of 10:2 vaccine:placebo. The ZPIV data also tracks with known correlates and surrogates of protection for currently licensed flavivirus vaccines. Completion of the studies is required to further define immune response durability and understand if current variations is response across study sites is maintained when data from all cohorts is collected and flavivirus primed and unprimed subsets are defined.

ZPIV was well tolerated and safe in a small number of volunteers and moderate to highly immunogenic. These data support proceeding to advanced clinical development.

Incorporation by Reference

All publications and patents mentioned herein are hereby incorporated by reference in their entirety as if each individual publication or patent was specifically and individually indicated to be incorporated by reference.

While specific aspects of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

REFERENCES

1. Hayes, E. B. (2009). "Zika Virus Outside Africa". *Emerging Infectious Diseases* 15 (9): 13471350. doi: 10. 3201/eid15O9. 090442. PMC 2819875. PMJD 19788800.
2. Darlington S (Dec. 23, 2015). "Brazil warns against pregnancy due to spreading virus". CNN. Retrieved Dec. 23, 2015.
3. Edelman R., et al., "Phase II safety and immunogenicity study of a live chikungunya virus vaccine," *Am. J. Trop. Med. Hyg.* 62(6): 681-5 (2000).
4. Harrison V. R., et al., "Production and evaluation of a formalin-killed chikungunya vaccine," *J. Immunol.* 107: 643-47 (1971).
5. Levitt N. H., et al., "Development of an attenuated strain of chikungunya virus for use in vaccine production," *Vaccine* 4(3): 157-62 (1986).
6. U.S. Pat. No. 6,254,873-Inactivated Dengue Virus Vaccine.
7. Canadian Patent CA 2452545 A1-West Nile Vaccine Comprising Live Attenuated, Inactivated or Killed Whole or Subunit West Nile Virus.
8. U.S. Pat. No. 8,741,312—High Yield Yellow Fever Virus Strain With Increased Propagation in Cells.
9. U.S. Patent Publication No. 2013/0022631 A1—Vaccine for Chikungunya Virus.
10. EP 1 724 338 A1-Methods for the production of a whole-inactivated West Nile Virus vaccine.
11. Canadian Patent CA 2301000 C—An attenuated Japanese encephalitis virus adapted to Vero cell and a Japanese encephalitis vaccine.
12. U.S. Pat. No. 6,309,650B1—Attenuated Japanese Encephalitis Virus Adapted to Vero Cell and a Japanese Encephalitis Vaccine.
13. A. S. Fauci, D. M. Morens, "Zika Virus in the Americas—Yet Another Arbovirus Threat," *N. Engl. J. Med.* 374: 601 (Feb. 18, 2016).
14. L. R. Petersen, D. J. Jamieson, A. M. Powers, M. A. Honein, Zika Virus. *N Engl. J. Med.* 374: 1552 (Apr. 21, 2016).
15. J. Mlakar et al., "Zika Virus Associated with Microcephaly," *N Engl. J. Med.* 374: 951 (Mar. 10, 2016).
16. P. Brasil et al., "Zika Virus Infection in Pregnant Women in Rio de Janeiro-Preliminary Report," *N Engl. J. Med.* (Mar. 4, 2016).
17. A. Rasmussen, D. J. Jamieson, M. A. Honein, L. R. Petersen, "Zika Virus and Birth Defects—Reviewing the Evidence for Causality," *N Engl. J. Med.* 374: 1981 (May 19, 2016).
18. A. Johansson, Y. T.-R. L. Mier, J. Reefhuis, S. M. Gilboa, S. L. Hills, "Zika and the Risk of Microcephaly," *N. Engl. J. Med.* 375: 2321-2334 (Dec. 15, 2016).
19. C. Li et al., "Zika Virus Disrupts Neural Progenitor Development and Leads to Microcephaly in Mice," *Cell Stem Cell* 19(1): 120-126 (May 9, 2016).
20. J. J. Miner et al., "Zika Virus Infection during Pregnancy in Mice Causes Placental Damage and Fetal Demise," *Cell* 165: 1081 (May 19, 2016).
21. F. R. Cugola et al., "The Brazilian Zika virus strain causes birth defects in experimental models," *Nature* 534: 267 (Jun. 9, 2016).
22. P. Brasil et al., "Guillain-Barre syndrome associated with Zika virus infection," *Lancet* 387: 1482 (Apr. 2, 2016).
23. W. Driggers et al., "Zika Virus Infection with Prolonged Maternal Viremia and Fetal Brain Abnormalities," *N. Engl. J. Med.* 374: 2142-2151 (Mar. 30, 2016).
24. D. M. Dudley et al., "A rhesus macaque model of Asian-lineage Zika virus infection," *Nature Communications* 7: 12204 (2016).
25. P. P. Garcez et al., "Zika virus impairs growth in human neurospheres and brain organoids," *Science* 352: 816 (May 13, 2016).
26. X. Qian et al., "Brain-Region-Specific Organoids Using Mini-bioreactors for Modeling ZIKV Exposure," *Cell* 165: 1238 (May 19, 2016).
27. R. A. Larocca et al., "Vaccine protection against Zika virus from Brazil," *Nature* 536: 474-478 (Jun. 28, 2016).
28. P. Abbink et al., "Construction and evaluation of novel rhesus monkey adenovirus vaccine vectors," *J. Virol.* 89: 1512 (February 2015).
29. K. E. Stephenson et al., "Quantification of the epitope diversity of HIV-1-specific binding antibodies by peptide microarrays for global HIV-1 vaccine development," *J. Immunol. Methods* 416: 105 (January 2015).
30. T. P. Endy et al., "Epidemiology of inapparent and symptomatic acute dengue virus infection: a prospective study of primary school children in Kamphaeng Phet, Thailand," *American J. Epidem.* 156: 40 (Jul. 1, 2002).
31. D. H. Libraty et al., "A prospective nested case-control study of Dengue in infants: rethinking and refining the antibody-dependent enhancement dengue hemorrhagic fever model," *PLoS Med.* 6: e1000171 (October, 2009).

32. G. Barba-Spaeth et al., "Structural basis of potent Zika-dengue virus antibody cross-neutralization," *Nature* 536(7614): 48-53 (Jun. 23, 2016).

33. Stettler et al., "Specificity, cross-reactivity and function of antibodies elicited by Zika virus infection," *Science* 353: 823-826 (Aug. 19, 2016).

34. W. Dejnirattisai et al., "Dengue virus sero-cross-reactivity drives antibody-dependent enhancement of infection with zika virus," *Nat. Immunol.* 17:1102-1108 (Jun. 23, 2016).

35. J. Hombach, T. Solomon, I. Kurane, J. Jacobson, D. Wood, "Report on a WHO consultation on immunological endpoints for evaluation of new Japanese encephalitis vaccines," WHO, Geneva, 2-3 Sep. 2004. *Vaccine* 23: 5205 (Nov. 1, 2005).

36. T. R. Kreil, I. Burger, M. Bachmann, S. Fraiss, M. M. Eibl, "Antibodies protect mice against challenge with tick-borne encephalitis virus (TBEV)-infected macrophages," *Clin. Exp. Immunol.* 110: 358 (December 1997).

37. R. A. Mason, N. M. Tauraso, R. O. Spertzel, R. K. Ginn, "Yellow fever vaccine: direct challenge of monkeys given graded doses of 17D vaccine," *Applied Microbiology* 25: 539 (April 1973).

38. L. J. Martinez et al., "Safety and Immunogenicity of a Dengue Virus Serotype-1 Purified-Inactivated Vaccine: Results of a Phase 1 Clinical Trial," *Am. J. Trop. Med. Hyg.* 93: 454 (September 2015).

39. S. Fernandez et al., "An adjuvanted, tetravalent dengue virus purified inactivated vaccine candidate induces long-lasting and protective antibody responses against dengue challenge in rhesus macaques," *Am. J. Trop. Med. Hyg.* 92: 698 (April 2015).

40. V. Demicheli, M. G. Debalini, A. Rivetti, "Vaccines for preventing tick-borne encephalitis," *The Cochrane Database of Systematic Reviews*, CD000977 (2009).

41. Demicheli, P. Graves, M. Pratt, T. Jefferson, "Vaccines for preventing tick-borne encephalitis," *Cochrane Database of Systematic Reviews*, CD000977 (2000).

42. E. O. Erra, A. Kantele, "The Vero cell-derived, inactivated, SA14-14-2 strain-based vaccine (Ixiaro) for prevention of Japanese encephalitis," *Expert Rev. Vaccines* 14: 1167 (2015).

What is claimed is:

1. A purified, inactivated, immunogenic Zika virus (ZIKV), wherein the purified, inactivated, immunogenic ZIKV is produced using a Zika virus strain, wherein the Zika virus strain is selected from the group consisting of: a purified, inactivated Puerto Rico PRVABC59 strain, a purified, inactivated Thailand SVO127/14 strain, a purified, inactivated Philippine COC C 0740 strain, and a purified, inactivated Brazil Fortaleza/2015 strain.

2. The purified, inactivated, immunogenic ZIKV of claim 1, wherein the ZIKV is produced using the purified, inactivated Puerto Rico PRVABC59 strain.

3. An immunogenic composition comprising the purified, inactivated, immunogenic ZIKV of claim 1 and a pharmaceutically acceptable adjuvant.

4. The immunogenic composition of claim 3, wherein the acceptable adjuvant is alum.

5. A vaccine comprising the purified, inactivated, immunogenic ZIKV of claim 1 and a pharmaceutically acceptable adjuvant.

6. The vaccine of claim 5, wherein the pharmaceutically acceptable adjuvant is alum.

7. The vaccine of claim 6, wherein the purified inactivated immunogenic ZIKV is produced using the purified, inactivated Puerto Rico PRVABC59 strain.

8. A method of producing antibodies which recognize ZIKV in a host comprising administering to the host a composition comprising the immunogenic composition of claim 3.

9. A method of inducing a protective immune response against a Zika virus (ZIKV) in a subject, comprising the step of administering to the subject the vaccine of claim 5.

10. The method of claim 9, wherein the administering is via an intramuscular injection, an intradermal injection, a subcutaneous injection, an intravenous injection, an oral administration, or an intranasal administration.

11. A method of treating or alleviating symptoms of ZIKV in a subject, comprising the step of administering to the subject the immunogenic composition of claim 3.

12. A medicament comprising the immunogenic composition of claim 3.

13. A medicament comprising the vaccine of claim 5.

14. A method of generating a purified inactivated ZIKV comprising the steps of:

i) inoculating a cell culture with an amount of a ZIKV strain;

ii) growing the inoculated virus in cell culture;

iii) harvesting and isolating virus fluids from the inoculated cell culture to prepare a Zika virus concentrate;

iv) purifying the ZIKV concentrate;

v) inactivating the purified ZIKV; and vi) recovering the purified, inactivated ZIKV.

15. The method of claim 14, wherein the purified ZIKV is inactivated by contacting the ZIKV with a chemical inactivating agent.

16. The method of claim 15, wherein the chemical inactivating agent is formalin, beta-propiolactone, or hydrogen peroxide.

17. The method of claim 15, wherein the ZIKV strain is selected from the group consisting of: Puerto Rico PRVABC59, Thailand SVO127/14, Philippine COC C 0740, or Brazil Fortaleza/2015, or other suitable strains.

* * * * *